(12) United States Patent
Noda

(10) Patent No.: US 8,172,455 B2
(45) Date of Patent: May 8, 2012

(54) LIQUID FEEDING METHOD AND CARTRIDGE TO BE USED THEREIN

(75) Inventor: Yuichiro Noda, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 867 days.

(21) Appl. No.: 12/084,215

(22) PCT Filed: Oct. 23, 2006

(86) PCT No.: PCT/JP2006/321019
§ 371 (c)(1),
(2), (4) Date: Apr. 28, 2008

(87) PCT Pub. No.: WO2007/049534
PCT Pub. Date: May 3, 2007

(65) Prior Publication Data
US 2009/0151792 A1 Jun. 18, 2009

(30) Foreign Application Priority Data
Oct. 28, 2005 (JP) ................................. 2005-315077

(51) Int. Cl.
*B01F 15/02* (2006.01)
*B01F 5/04* (2006.01)
(52) U.S. Cl. ............... 366/173.1; 366/177.1; 366/182.2; 366/341
(58) Field of Classification Search ............ 137/14; 366/163.1, 177.1, 182.2, 191, 341, DIG. 1–DIG. 3
See application file for complete search history.

(56) References Cited

U.S. PATENT DOCUMENTS

| 4,550,681 | A | * | 11/1985 | Zimmer et al. | 118/410 |
|---|---|---|---|---|---|
| 4,624,928 | A | | 11/1986 | Qureshi | |
| 5,071,562 | A | * | 12/1991 | Allington et al. | 210/656 |
| 5,230,866 | A | | 7/1993 | Shartle et al. | |
| 5,587,128 | A | * | 12/1996 | Wilding et al. | 422/50 |
| 5,716,852 | A | * | 2/1998 | Yager et al. | 436/172 |
| 5,839,467 | A | * | 11/1998 | Saaski et al. | 137/501 |
| 5,932,100 | A | * | 8/1999 | Yager et al. | 210/634 |
| 5,967,167 | A | * | 10/1999 | Johnson | 137/14 |
| 5,971,158 | A | * | 10/1999 | Yager et al. | 209/155 |
| 5,974,867 | A | * | 11/1999 | Forster et al. | 73/61.41 |
| 6,065,864 | A | * | 5/2000 | Evans et al. | 366/167.1 |
| 6,110,343 | A | * | 8/2000 | Ramsey et al. | 204/601 |
| 6,150,119 | A | * | 11/2000 | Kopf-Sill et al. | 435/7.1 |
| 6,167,910 | B1 | * | 1/2001 | Chow | 137/827 |
| 6,168,948 | B1 | * | 1/2001 | Anderson et al. | 435/287.2 |
| 6,192,939 | B1 | * | 2/2001 | Yao et al. | 138/39 |
| 6,213,151 | B1 | * | 4/2001 | Jacobson et al. | 137/827 |

(Continued)

FOREIGN PATENT DOCUMENTS
EP 1 203 959 5/2002
(Continued)

*Primary Examiner* — Tony G Soohoo
(74) *Attorney, Agent, or Firm* — Fox Rothschild LLP

(57) ABSTRACT

A liquid feeding method for feeding liquid in a minute flow path is provided. The minute flow path includes flow paths 43a, 43c, 43d connected to each other directly at respective first ends. The liquid feeding direction of blood S in the minute flow path is controlled by creating a high-pressure state at a second end of the flow path 43a located across the blood S, while creating a low-pressure state or a closed state at a second end of the flow paths 43d, 43c.

8 Claims, 32 Drawing Sheets

U.S. PATENT DOCUMENTS

| | | | |
|---|---|---|---|
| 6,221,654 B1 * | 4/2001 | Quake et al. | 435/287.3 |
| 6,244,738 B1 * | 6/2001 | Yasuda et al. | 366/114 |
| 6,270,641 B1 * | 8/2001 | Griffiths et al. | 204/451 |
| 6,296,020 B1 | 10/2001 | McNeely et al. | |
| 6,615,856 B2 * | 9/2003 | McNeely et al. | 137/14 |
| 6,623,860 B2 * | 9/2003 | Hu et al. | 428/411.1 |
| 7,293,720 B2 * | 11/2007 | Ramsay | 239/76 |
| 7,329,391 B2 * | 2/2008 | Cox | 422/503 |
| 7,485,266 B2 * | 2/2009 | Ito et al. | 422/224 |
| 2001/0055242 A1 * | 12/2001 | Deshmukh et al. | 366/341 |
| 2002/0036018 A1 | 3/2002 | McNeely et al. | |
| 2002/0075363 A1 | 6/2002 | McNeely et al. | |
| 2002/0172617 A1 | 11/2002 | Biwa et al. | |
| 2002/0174891 A1 * | 11/2002 | Maluf et al. | 137/14 |
| 2003/0044322 A1 * | 3/2003 | Andersson et al. | 422/100 |
| 2004/0109793 A1 | 6/2004 | McNeely et al. | |
| 2004/0265184 A1 | 12/2004 | Matsuda et al. | |
| 2005/0092681 A1 * | 5/2005 | Higashino et al. | 210/634 |
| 2005/0148091 A1 | 7/2005 | Kitaguchi et al. | |
| 2005/0202504 A1 | 9/2005 | Anderson et al. | |
| 2008/0314454 A1 * | 12/2008 | Delattre et al. | 137/14 |
| 2009/0123337 A1 * | 5/2009 | Noda et al. | 422/73 |

FOREIGN PATENT DOCUMENTS

| | | |
|---|---|---|
| JP | 2002-527250 | 8/2002 |
| JP | 2003-194827 | 7/2003 |
| JP | 2005-513441 | 5/2005 |
| WO | WO 01/13127 | 2/2001 |
| WO | WO 01/88204 | 11/2001 |
| WO | WO 2006137431 A1 * | 12/2006 |

\* cited by examiner

LIQUID FEEDING METHOD AND CARTRIDGE TO BE USED THEREIN

TECHNICAL FIELD

The present invention relates to a liquid feeding method for feeding liquid in a minute flow path, while also relating a cartridge to be used for the method.

BACKGROUND ART

The analysis of a particular component in blood is widely performed to check the condition of a human body. In recent years, such analysis of a particular component is performed using a relatively compact analyzer instead of using a large apparatus. To reduce the size of such an analyzer, the flow path in the analyzer needs to be made as small as possible, and a technique is necessary to properly feed blood or other kind of liquid through the flow path.

FIG. 40 shows an example of liquid feeder for a conventional liquid feeding method. The liquid feeder X shown in the figure includes an analysis portion 91, a heater 92, a minute flow path 93, a plurality of valves 94 and a liquid pooling tank 95. The heater 92 heats blood or other kind of liquid. The heated liquid is injected into an introduction port 93i of the minute flow path 93 shown in the left side in the figure. In flowing through the minute flow path 93 or the liquid pooling tank 95, the liquid may be diluted to a concentration suitable for the analysis or mixed with a reagent. The sample liquid obtained by such dilution or mixing is fed into the analysis portion 91 through a discharge port 93o. In the analysis portion 91, the analysis of a particular component by e.g. optical means is performed. The sample liquid after the analysis is introduced again into the minute flow path 93 thorough the introduction port 93i shown in the right side in the figure and then discharged to e.g. a non-illustrated drain. In the liquid feeder X, the start and stop of the liquid feeding in the minute flow path 93 and the selection of the liquid feeding direction from a branch portion are performed by utilizing the valves 94 provided in the minute flow path 93 along the flow direction. Each of the valves 94 is rotatable and switched between a closed state, an open state and a state to control the liquid flow to a certain direction by a rotation drive means (not shown) provided in the analyzer X. Thus, by properly arranging the valves 94 in the minute flow path 93, the liquid is fed in a desired direction.

When the system for analyzing e.g. blood is made up of an analyzer and a cartridge to be mounted to the analyzer, the minute flow path 93 and the valves 94 need to be provided in the cartridge. The provision of the valves 94, which are rotatable parts, complicates the structure of the cartridge. Particularly, since the leakage of blood or other kind of liquid from the slidable portions of the valves 94 needs to be prevented, the manufacturing of the cartridge is difficult. Further, to reduce the size of such a cartridge is difficult. To frequently perform the analysis of a particular component in blood conveniently, the size reduction of a cartridge is essential. Further, since the above-described analyzer requires the rotation drive means for rotating the valves 94, the structure of the analyzer is complicated and the size is increased.

Patent Document 1: U.S. Pat. No. 4,624,928

DISCLOSURE OF THE INVENTION

The present invention is proposed under the above-described circumstances. It is, therefore, an object of the present invention to provide a liquid feeding method capable of properly and accurately feeding liquid with the use of an apparatus having a relatively simple structure, and to provide a cartridge used for the method.

To solve the above-described problems, the present invention takes the following technical measures.

According to a first aspect of the present invention, there is provided a liquid feeding method for feeding liquid in a minute flow path including at least three flow paths having respective first ends connected to each other directly or indirectly via a connection flow path. The method comprises: introducing the liquid; creating a high-pressure state at a second end of at least one of at least three flow paths mentioned above; and creating a low-pressure state or a closed state at second ends of remaining flow paths, thereby controlling a liquid feeding direction of the liquid in the minute flow path.

Preferably, the second ends of at least two of at least three flow paths may be held in a high-pressure state or a closed state.

Preferably, the minute flow path may have an inner surface which is hydrophobic with respect to the liquid.

Preferably, the inner surface of the minute flow path may have a contact angle of not less than 60 degrees with the liquid.

Preferably, one of the high-pressure state and the low-pressure state at the minute flow path may be a state of atmospheric pressure.

According to a second aspect of the present invention, there is provided a cartridge to be mounted to a separate apparatus. The cartridge comprises a minute flow path for feeding liquid, where the minute flow path includes at least three flow paths having respective first ends connected to each other directly or indirectly via a connection flow path, and each of the flow paths has a second end connected to a hole.

Preferably, the minute flow path may have an inner surface which is hydrophobic with respect to the liquid.

Preferably, the inner surface of the minute flow path may have a contact angle of not less than 60 degrees with the liquid.

Other features and advantages of the present invention will become more apparent from the detailed description given below with reference to the accompanying drawings.

BEST MODE FOR CARRYING OUT THE INVENTION

Preferred embodiments of the present invention will be described below with reference to the accompanying drawings.

FIGS. 1 and 2 show an analyzer cartridge according to a first embodiment of the present invention. The illustrated cartridge A1 includes a main body 1, and a printed wiring board 2 bonded to the main body. The cartridge further includes dilution means 4, a plurality of analysis portions 5A, 5B, 5C, 5D and two flow measuring units 6A and 6B.

The main body 1 has a flat rectangular configuration and is made of a transparent resin such as an acrylic resin. The lower surface of the main body 1 in FIG. 1 is formed with a plurality of recesses or grooves for forming flow paths or tanks, which will be described later. As shown in FIG. 1, the main body 1 is further formed with a plurality of holes H1-H14 penetrating the main body in the thickness direction. In this embodiment, the main body 1 is about 70 mm square and has a thickness of about 5 mm.

The printed wiring board 2 is formed by laminating a plurality of substrates made of e.g. an epoxy resin. A wiring pattern made of e.g. a copper foil is provided between the substrates. The printed wiring board 2 is formed with a plurality of electrodes 51 and 62, which will be described later. These electrodes 51 and 62 have a through-hole structure. A connector 8 is provided at an extension of the printed wiring board 2. The connector 8 is used for connecting the cartridge A1 to an analyzer such as a blood cell counter (not shown). The main body 1 and the printed wiring board 2 are liquid-tightly bonded to each other with e.g. an adhesive. The main body 1 and the printed wiring board 2 have a hydrophobic surface having a contact angle with blood of not less than 60 degrees at least at portions forming the flow paths, which will be described below.

The hole H1 serves as a liquid introduction port for introducing blood to be analyzed into the cartridge A1. The hole H1 has a diameter of about 3 mm. As shown in FIG. 3, the hole H1 penetrates the main body 1, and the lower portion of the hole in the figure is connected to an introduction flow path 43a.

The dilution means 4 dilutes the blood introduced from the hole H1 to a concentration suitable for various kinds of analysis. The dilution means 4 includes a first and a second diluent tanks 41A, 41B, a first and a second dilution tanks 42A, 42B, a blood measurer 43, a first and a second diluent measurer 44A, 44B and a first blood sample measurer 45. The dilution means 4 of this embodiment can perform two-stage dilution using the first and the second dilution tanks 42A and 42B, which will be described later.

The first and the second diluent tanks 41A and 41B serve to store diluents 40A and 40B for diluting blood within the cartridge A1. Both of the diluent tanks 41A and 41B have a diameter of about 12 mm and a depth of about 3 mm and are capable of storing about 200 µL of diluent 40A, 40B. As the diluents 40A and 40B, use may be made of physiological salt solution, for example. To store the diluents 40A and 40B in the diluent tanks 41A and 41B, use may be made of an aluminum bag having a shape conforming to the inner surface of the first and the second diluent tanks 41A and 41B.

The blood measurer 43 is arranged between the hole H1 and the first dilution tank 42A and includes an introduction flow path 43a, a measurement flow path 43c, and an overflow path 43d. The introduction flow path 43a is used for introducing blood from the hole H1. The measurement flow path 43c and the overflow path 43d extend from the introduction flow path 43a via a branch portion 43b. The measurement flow path 43c is used for temporarily retaining the blood by an amount suitable for the analysis. Each of the introduction flow path 43a, the measurement flow path 43c and the overflow path 43d has a width of about 380 µm and a depth of 380 µm, so that the width/depth is one. The measurement flow path 43c has a length of about 8 mm and a volume of about 0.5 µL. An orifice 43e is provided between the measurement flow path 43c and the first dilution tank 42A. The orifice 43e has a width of about 50 µm and is provided for intentionally increasing the pressure drop resistance from the measurement flow path 43c to the first dilution tank 42A. The overflow path 43d includes a plurality of bent portions and is connected to the hole 8.

The first diluent measurer 44A is arranged downstream from the first diluent tank 41A and connected to the first dilution tank 42A. The first diluent measurer 44A includes an introduction flow path 44Aa, a measurement flow path 44Ac and an overflow path 44Ad. The introduction flow path 44Aa is utilized for introducing the diluent 40A from the first diluent tank 41A and has a width of about 200 µm and a depth of about 200 µm. Unless otherwise described, each of the flow paths described below has the same width and depth as those of the introduction flow path 44Aa. To achieve uniform flow in each of the flow paths, it is preferable that the width/depth is not more than five. The measurement flow path 44Ac extends from the introduction flow path 44Aa via a branch portion 44Ab. Another flow path extending from the branch portion 44Ab is connected to the hole H4. The measurement flow path 44Ac is used for temporarily retaining a precise amount of diluent 40A. As shown in FIGS. 4 and 5, the measurement flow path 44Ac includes a large cross-sectional portion 44Aca and two tapered portions 44Acb. The large cross-sectional portion 44Aca has a width of about 2 mm and a depth of about 2 mm, and the volume is about 50 µL. The two tapered portions 44Acb are connected respectively to the front end and the rear end of the large cross-sectional portion 44Aca and prevent the flow of the diluent 40A into and out of the large cross-sectional portion 44Aca from being disturbed. The overflow path 44d is connected to the hole H6 as shown in FIG. 2 and has a width and a depth of about 1 mm.

The second diluent measurer 44B is arranged downstream from the second diluent tank 41B and connected to the second dilution tank 42B. The second diluent measurer 44B includes an introduction flow path 44Ba, a measurement flow path 44Bc, and an overflow path 44Bd. The dimension and relationship with the holes H5, H7 of each part of the second diluent measurer 44B are the same as those in above-described first diluent measurer 44A.

The first and the second dilution tanks 42A and 42B are used for diluting blood and have a diameter of about 6 mm, a depth of about 2 mm and a volume of not less than 50 µL. The first dilution tank 42A is connected to the blood measurer 43 and the first diluent measurer 44A. The blood measured by the blood measurer 43 is diluted in the first dilution tank with the diluent 40A measured by the first diluent measurer 44A. The second dilution tank 42B is connected to the second diluent measurer 44B and the first blood sample measurer 45. The first blood sample measured by the first blood sample measurer 45 is diluted in the second dilution tank 42B with the diluent 40B measured by the second diluent measurer 44B.

The first blood sample measurer 45 includes an introduction flow path 45a, a measurement flow path 45c, and an overflow path 45d. The measurement flow path 45c and the overflow path 45d are connected to the introduction flow path 45a via a branch portion 45b. The measurement flow path 45a is connected to the second dilution tank 42B via an orifice 45e. The overflow path 45d includes a downstream portion having a width and a depth of about 0.5 mm. The downstream end of the overflow path 45d is connected to the hole H10.

The analysis portions 5A, 5B, 5C and 5D are provided for performing the analysis of a particular component in the blood. The first and the second analysis portions 5A and 5B are designed to perform the analysis by electrical resistance measurement. The first analysis portion 5A is for white blood cells, whereas the second analysis portion 5B is for red blood cells. The third and the fourth analysis portions 5C and 5D are designed to perform analysis by an optical method. The third analysis portion 5C is for Hb, whereas the fourth analysis portion is for CRP.

The first analysis portion 5A is connected to the first dilution tank 42A via a buffer tank 46. The white blood cells are counted in the first analysis portion 5A by using the blood sample diluted in the first dilution tank 42A. The hole H9 is connected to a portion between the buffer tank 46 and the first dilution tank 42A via a branch flow path. As shown in FIGS. 6 and 7, the first analysis portion 5A includes a minute hole 52 and a pair of electrodes 51 arranged on the opposite sides of the minute hole 52 to perform the analysis by electrical resistance measurement. While the width of the flow path on the opposite sides of the minute hole 52 is about 200 µm, the minute hole 52 has a relatively small width of about 50 µm.

This width is so determined that the electrical resistance between the paired electrodes 51 changes considerably when a white blood cell passes through the minute hole. The flow path includes portions enlarged into a generally circular shape on the opposite sides of the minute hole 52, at which the paired electrodes 51 are provided. The paired electrodes 51 are formed by printing using one or a plurality of materials selected from gold, platinum, palladium and carbon, for example. As shown in FIG. 7, each of the electrodes 51 is electrically connected to a wiring pattern 22 via a through-hole 53. The through-hole 53 and the wiring pattern 22 may be made of copper, for example.

As shown in FIG. 2, the second analysis portion 5B is connected to the second dilution tank 42B. The red blood cells are counted in the second analysis portion 5B by using the blood sample after the second dilution in the second dilution tank 42B. The structure of the second analysis portion 5B is substantially the same as that of the first analysis portion 5A described with reference to FIGS. 6 and 7.

Each of the third and the fourth analysis portions 5C and 5D is independently connected to the buffer tank 46. As shown in FIGS. 8 and 9, each of the third and the fourth analysis portions 5C and 5D includes a reflection film 55 provided at a portion of the flow path which is enlarged into a generally circular shape. The third and the fourth analysis portions are designed to measure Hb and CRP, respectively, by an optical method. The reflection films 55 are formed collectively with the electrodes 51 by printing using one or a plurality of materials selected from gold, platinum and palladium, for example. As shown in FIG. 9, a reagent 56 is applied to the upper surface of the enlarged portion of the flow path. By mixing the blood sample with the reagent 56, the measurement of Hb or CRP by an optical method is performed. In this embodiment, light impinges on the third and the fourth analysis portions 5C and 5D through the main body 1, which is transparent. By detecting the reflected light, Hb and CRP are measured. The holes H13 and H14 are arranged on the downstream side of the third and the fourth analysis portions 5C and 5D.

The first and the second flow measuring units 6A and 6B are connected to the first and the second analysis portions 5A and 5B, respectively. The flow measuring units 6A and 6B measure the flow of the blood sample through the first and the second analysis portions 5A and 5B, respectively. Each of the flow measuring units includes a meandering flow path 61 and two electrodes 62. The meandering flow path 61 is provided to increase the length in the flow direction and has a sufficient volume. The width and depth of the meandering flow path is about 1 mm. In this embodiment, the meandering flow path 61 serves as a storage means capable of storing at least 50 µL of blood sample after the analysis at the first or the second analysis portion 5A or 5B. The two electrodes 62 are spaced from each other in the flow direction of the meandering flow path 61. Each of the electrodes 62 has the substantially same structure as that of the electrode 51. The holes H11 and H12 are arranged on the downstream side of the first and the second flow measuring units 6A and 6B.

The blood analysis using the cartridge A1 will be described below.

First, referring to FIGS. 1 and 2, blood as the sample liquid is introduced from the hole H1 by using e.g. a dropper. Then, the cartridge A1, into which blood is introduced, is mounted to an analyzer (not shown). Specifically, the cartridge is mounted by connecting the connector 8 to a connector (now shown) of the analyzer. In this process, the holes H1-H14 are connected to a valve unit connected to a pump in the analyzer. By the operation of the pump and the valve unit, the analyzer causes each of the holes H1-H14 to independently undergo pressure increase due to air application, or pressure drop due to exposure to the atmospheric pressure.

Then, the blood is measured by the blood measurer 43. This process will be described below with reference to FIGS. 10-12. Since the main body 1 and the printed wiring board 2 have hydrophobic surfaces relative to blood, the blood S introduced through the hole H1 does not flow due to the capillary action but remains in the hole H1. After the blood S is introduced, air application is performed through the hole H1, whereas the holes H8 and H9 are exposed to atmospheric pressure, as shown in FIG. 10. As a result of this operation, the hole H1 side is held in a high-pressure state, whereas the holes H8, H9 side is held in a low-pressure state. Thus, the blood S starts to flow from the hole H1 to the measurement flow path 43c and the overflow path 43d through the introduction flow path 43a. Since the cross-sectional area of the measurement flow path 43c and that of the overflow path 43d are substantially equal to each other, the pressure drop resistance during the flow of the blood S is substantially equal to each other. Thus, the blood S moves substantially the same distance through each of the measurement flow path 43c and the overflow path 43d. With the air application maintained, the measurement flow path 43c is filled with the blood S, as shown in the figure. When the measurement flow path 43c is filled with the blood, the blood S is present in the overflow path 43d by an amount corresponding to the length of the measurement flow path 43c. It is to be noted that an arrow in the figure pointing toward the center of a hole indicates that the opening is in a high-pressure state (H1), whereas an arrow pointing outward from a hole indicates that the opening is in a low-pressure state (H8, H9). This holds true for the subsequent figures.

The air application is continued further from the state shown in FIG. 10, and the state shown in FIG. 11 is obtained. Specifically, since the orifice 43e is provided on the downstream side of the measurement flow path 43c, the pressure drop resistance when the blood S flows is very large. On the other hand, the overflow path 43d has a uniform cross-sectional area in the flow direction, so that the pressure drop resistance is considerably smaller than that in the orifice 43e. Thus, with the blood S retained within the measurement flow path 43c, the blood S continues to flow through the overflow path 43d. After a while, all the blood S flows out of the hole H1. As shown in the figure, due to the continuation of the air application, air is introduced into the introduction flow path 43a and the upstream portion of the overflow path 43d instead of the blood S. Thus, the blood Sa retained in the measurement flow path 43c is separated from the blood S. The amount of blood S injected into the hole H1 is generally constant, so that the time taken from the start of air application shown in FIG. 10 until the state shown in FIG. 11 is obtained is generally constant. Thus, this time is measured using a timer provided in the analyzer, and the air application is stopped after the lapse of this time.

Then, as shown in FIG. 12, with the hole H8 closed by the analyzer, air is applied again through the hole H1. As a result, the blood Sa retained in the measurement flow path 43c flows into the first dilution tank 42A through the orifice 43e. By the above-described process, the measurement of a predetermined amount of blood Sa is completed, and the predetermined amount, i.e., about 0.5 µL of blood Sa is retained in the first dilution tank 42A.

The process of measuring the diluent 40A by the first diluent measurer 44A will be described below with reference to FIGS. 13 and 14. FIG. 13 shows the state to start the measurement of the diluent 40A. To provide this state, an aluminum bag (not shown) containing the diluent 40A is broken within the first diluent tank 41A to make the diluent 40A ready to flow out. Since the main body 1 and the printed wiring board 2 have hydrophobic surfaces, the diluent 40A does not unduly flow out due to the capillary action even when the aluminum bag is broken.

After the diluent 40 is made ready to flow out, the application of air through the hole H2 is started, with the holes H4 and H9 closed and the hole H6 exposed to atmospheric pressure. As a result, the diluent 40A is pushed out of the first diluent tank 41A and flows into the measurement flow path 44Ac through the introduction flow path 44Aa. The measurement flow path 44Ac includes a large cross-sectional portion 44Aca on the downstream side of a tapered portion 44Acb. As noted before, since the surface forming the large cross-sectional portion 44Aca is hydrophobic, the surface tension to retain the diluent 40A within the upper portion in the figure acts on the diluent. Thus, the flow of diluent due to the capillary action does not occur. Due to the motive force caused by the above-described air application, the diluent 40A gradually flows downward in the figure against the surface tension. When the air application is continued, the diluent 40A fills the measurement flow path 44Ac and flows toward the overflow path 44Ad. When the front of the diluent 40A reaches a predetermined position in the overflow path 44Ad, this fact is detected by electrical resistance means using an e.g. electrode (not shown) or an optical means using a reflection film (not shown). When this is detected, the air application is stopped.

Then, as shown in FIG. 14, with both of the holes H2 and H6 closed and the hole H9 exposed to the atmospheric pressure, air is applied through the hole H4. As a result, the diluent 40A retained in the measurement flow path 44Ac flows into the first dilution tank 42A. By this process, the measurement of the diluent 40A is completed, and a predetermined amount, i.e., about 50 μL of diluent 40Aa is retained in the first dilution tank 42A.

Then, about 0.5 μL of blood Sa and about 50 μL of diluent 40Aa are mixed within the first dilution tank 42A to provide blood sample as a 1:100 diluted sample liquid. The mixing may be performed by rotating a stirrer incorporated in the first dilution tank 42A by magnetic force. The above-described dilution is hereinafter referred to as the first dilution.

After the first dilution in the first dilution tank 42A is completed, the white blood cells are counted in the first analysis portion 5A, and Hb and CRP are measured in the third and the fourth analysis portions 5C and 5D. This process will be described below with reference to FIGS. 15-18. As shown in FIG. 15, the buffer tank 46 is connected to the first dilution tank 42A. With the hole H11 exposed to atmospheric pressure, air is applied through the hole H4 shown in FIG. 1, for example. As a result, as shown in FIG. 15, the 1:100 diluted first blood sample DS1 flows into the buffer tank 46. To count white blood cells, the first blood sample DS needs to be subjected to hemolytic treatment to destroy the red blood cells contained in the blood sample. In this embodiment, hemolytic agent is applied to the buffer tank 46, for example.

The white blood cells are counted in the first analysis portion 5A using part of the first blood sample DS stored in the buffer tank 46. This counting is performed using the first analysis portion 5A and the first flow measuring unit 6A positioned on the downstream side of the first analysis portion. As shown in FIG. 16, with the hole H11 exposed to atmospheric pressure, air is applied through the hole H9. As a result, the first blood sample DS1 flows out of the buffer tank 46 to flow into the first analysis portion 5A. The front of the first blood sample DS1 reaches the electrode 62 positioned on the upstream side. The fact that the front of the blood sample DS1 has reached the electrode 62 on the upstream side can be detected by monitoring the electrical conduction between the electrode 62 and the electrode 51, for example. Based on this detection, the counting of white blood cells by the first analysis portion 5A is started. Since the minute hole 52 has a small width as noted before, the electrical resistance between the paired electrodes 51 instantaneously increases when a white blood cell passes through the minute hole. Thus, by performing time-series monitoring of the electrical resistance between the paired electrodes 51, pulses generated correspondingly to the passage of white blood cells are detected. The number of the pulses is integrated.

When the application of air is continued while integrating the pulses, the front of the first blood sample DS1 reaches the electrode 62 on the downstream side, as shown in FIG. 17. The fact that the front of the blood sample has reached this electrode can be detected by monitoring the electrical conduction between the two electrodes 62, for example. When the reaching is detected, the air application through the hole H9 is stopped, and the counting by the first analysis portion 5A is finished. The amount of the first blood sample DS1 which passes through the first analysis portion 5A during the period from when the front of the first blood sample DS1 reaches the electrode 62 on the upstream side until when the front reaches the electrode 62 on the downstream side is equal to the amount of the first blood sample DS1 which can be retained between the electrodes 62. Since the distance between the two electrodes 62 along the flow direction is known, the amount of the first blood sample DS1 which has passed through the first analysis portion 5A is found properly. Based on this amount and the number of pulses integrated, the number of white blood cells per unit volume of the first blood sample DS1 is found, based on which the number of white blood cells per unit volume of the blood S is determined. As will be understood from the figure, when the counting by the first analysis portion 5A is finished, the first blood sample DS1 after the analysis remains in the meandering flow path 61.

As shown in FIG. 18, after the counting by the first analysis portion 5A is finished, the analysis by the third and the fourth analysis portions 5C and 5D is performed. Specifically, with the holes H13, H14 exposed to atmospheric pressure, air is applied through the hole H9. As a result, the first blood sample DS1 reaches the respective reflection films 55 of the third and the fourth analysis portions 5C and 5D. The first blood sample DS1 reacts with the reagent 56 shown in FIG. 9 to become ready for the analysis of Hb or CRP. In this state, light is directed from the analyzer onto each of the reflection films 55 through the main body 1, and the reflected light is received by e.g. a light receiving element provided in the analyzer through the main body 1. By processing the received light appropriately, the analysis of Hb and CRP is performed. Unlike this embodiment, the printed wiring board 2 may be replaced with a substrate made of a transparent material. In this case, the reflection films 55 are unnecessary, and each of the third and the fourth analysis portions 5C and 5D is sandwiched between the main body 1 and the substrate both of which are transparent. With this arrangement, the analysis of Hb and CRP can be performed by the transmission measurement.

The second dilution process will be described below with reference to FIGS. 19-23. First, as shown in FIG. 19, with the hole H10 exposed to atmospheric pressure, air is applied through the hole H9. In this process, the holes H5, H7 and H12 are kept closed. As a result, the first blood sample DS1 flows from the first dilution tank 42A into the overflow path 45d through the introduction flow path 45a. The application of air through the hole H9 is continued until the front of the first blood sample DS1 passes through the narrow portion of the introduction flow path 45a and reaches the wide portion. The fact that the front of the first blood sample DS1 has reached the wide portion of the overflow path 45d may be detected by an electrical means using an electrode (not shown) provided in the overflow path 45d or an optical means using a reflective film (not shown).

As shown in FIG. 20, after the fact that the first blood sample DS1 has reached the wide portion of the overflow path 45d is detected, the hole H12 is exposed to atmospheric pressure. As a result, the first blood sample DS1 flows through the overflow path 45d and the measurement flow path 45c. Since the narrow portion of the overflow path 45d meanders as illustrated, the pressure loss is relatively large. However, by causing the first blood sample DS1 to reach the wide portion of the overflow path 45d in advance, the first blood sample DS1 has affinity with the narrow portion of the overflow path 45d. Thus, in the state shown in FIG. 20, the first blood sample DS1 flows smoothly through both of the overflow path 45d and the measurement flow path 45c. When the application of air through the hole H9 is continued, all of the first blood sample DS1 flows out of the first dilution tank 42A, and the introduction flow path 45a and the narrow portion and the upstream side of the wide portion of the overflow path 45d are filled with air from the hole H9. In this state, a predetermined amount of first blood sample DS1a is separated and retained in the measurement flow path 45c.

The fact that air has reached the wide portion of the overflow path 45d is detected by an electrical means or an optical means. Based on the detection, the hole H10 is closed, as shown in FIG. 21. As a result, the first blood sample DS1a retained in the measurement flow path 45c is pushed out into the second dilution tank 42B. Thus, the predetermined amount of, i.e., about 0.5 μL of first blood sample DS1a is retained in the second dilution tank 42B.

Then, the measurement of the diluent 40B is performed by the second diluent measurer 44B. This measurement is performed similarly to the measurement of the diluent 40A by the first diluent measurer 44A. Specifically, as shown in FIG. 22, air is applied through the hole H3, with the hole H7 exposed to atmospheric pressure. As a result, the diluent 40B retained in the second diluent tank 41B flows into the measurement flow path 44Bc and the overflow path 44Bd.

As shown in FIG. 23, after the flow of the diluent 40B into the overflow path 45Bd is detected, air is applied through the opening H5, with the opening H7 closed and the opening H12 exposed to atmospheric pressure. As a result, the diluent 40B retained in the measurement flow path 44Bc flows into the second dilution tank 42B. As a result, 0.5 μL of first blood sample DS1a and 50 μL of diluent 40Ba are retained in the second dilution tank 42B. Then, the first blood sample DS1a and the diluent 40Ba are stirred by rotating a stirrer (not shown) incorporated in the second dilution tank 42B. As a result, the second dilution to dilute the blood S substantially 1:10000 is completed.

Then, the red blood cells are counted by the second analysis portion 5B. The counting is performed in a substantially same manner as the counting by the first analysis portion 5A. As shown in FIG. 24, the second blood sample DS2 obtained by the above-described second dilution is retained in the second dilution tank 42B. With the hole H12 exposed to atmospheric pressure, air is applied through e.g. the opening H5 shown in FIG. 2. As a result, the second blood sample DS2 passes through the second analysis portion 5B to reach the electrode 62 on the upstream side. From this time point, counting of red blood cells by the second analysis portion 5B is started. When the fact that the second blood sample DS2 has reached the electrode 62 on the downstream side as shown in FIG. 25 is detected, the application of air through the hole H5 shown in FIG. 2 is stopped, and the counting of red blood cells by the second analysis portion 5B is finished. The flow measurement by the second flow measuring unit 6B is performed similarly to the flow measurement by the first flow measuring unit 6A.

The advantages of the cartridge A1 will be described below.

According to this embodiment, by appropriately switching the holes H1-H14 between a high-pressure state, a low-pressure state and a closed state, the blood S, the first and the second blood samples DS1, DS2 or the diluents 40A, 40B flows in a desired direction through a minute flow path formed in the main body 1 without the need for providing e.g. a rotary valve in the cartridge A1. Thus, the size of the cartridge A1 is reduced, and the structure is simplified. Further, since the cartridge A1 does not need to include a driving portion such as a valve, the process for manufacturing the cartridge A1 does not involve a troublesome work of e.g. making part of the cartridge liquid-tightly slidable. Thus, the process for manufacturing the cartridge A1 is relatively simple, which leads to a reduction in the manufacturing cost. Thus, the cartridge A1 can be suitably used as a disposable cartridge which enables the user to frequently perform e.g. blood analysis with less economic burden.

In the analysis described above, although the blood S is injected into the cartridge A1, no liquid is discharged from the cartridge A1. Thus, the cartridge A1 after the use for analysis can be just disposed of, and the treatment of waste liquid such as the first and the second blood samples DS1 and DS2 is not necessary. Moreover, the analyzer to which the cartridge A1 is mounted does not get wet and is kept dry, so that the analyzer for analyzing e.g. blood and the surroundings are kept hygienic.

In the blood measurer 43, the first and the second diluent measurers 44A, 44B and the first blood sample measurer 45 and so on included in the dilution means 4, the blood S or the first and the second blood samples DS1, DS2 properly flows from a single flow path into a plurality of flow paths branching from the single flow path. Further, when the application of air is not performed, the liquid is stopped. By the combination of the flow and stop of the liquid, the dilution means 4 properly performs the two-stage dilution.

FIGS. 26-40 show other embodiments of an analyzer cartridge according to the present invention. In these figures, the elements which are identical or similar to those of the foregoing embodiment are designated by the same reference signs as those used for the foregoing embodiment, and the description is omitted appropriately.

FIG. 26 shows an analyzer cartridge according to a second embodiment of the present invention. The cartridge A2 of this embodiment differs from that of the first embodiment in structure of the dilution means 4. In this embodiment, the dilution means 4 includes a diluent tank 41, a diluent measurer 44 and a first blood sample measurer 45.

The diluent tank 41 for storing diluent 40 is similar to the first and the second diluent tanks 41A, 41B of the first embodiment. The diluent measurer 44 includes an introduction flow path 44Aa, a branch portion 44b, a measurement flow path 44c and a first and a second overflow paths 44Ad, 44Bd. The first and the second overflow paths 44Ad and 44Bd are connected to the downstream side of the measurement flow path 44c. Holes H6 and H7 are arranged on the downstream side of the first and the second overflow paths 44Ad and 44Bd, respectively. The branch portion into the first overflow path 44Ad is located closer to the measurement flow path 44c than the branch portion into the second overflow path 44Bd is.

Similarly to the first embodiment, the first blood sample measurer 45 includes an introduction flow path 45a, a measurement flow path 45c and an overflow path 45d. In this embodiment, however, the measurement flow path 45c is connected to a substantially middle position of the flow path extending from the measurement flow path 44c to the first dilution tank 42A. The flow path extending from the position to which the measurement flow path 45c is connected to the first dilution tank 42A is defined as the introduction flow path 45a. The branch portion into the overflow path 45d is located between the branch portion into the first overflow path 44Ad and the branch portion into the second overflow path 44Bd.

The blood analysis using the cartridge A2 will be described below. The blood analysis method according to this embodiment differs from that using the cartridge A1 of the first embodiment in dilution step using the dilution means 4. The dilution step using the dilution means 4 will be described below.

FIG. 27 shows the state to start the dilution step using the dilution means 4. Before the dilution step, a predetermined amount of blood Sa is measured out and retained in the first dilution tank 42A. This measurement of the blood Sa is performed in advance by the blood measurer 43 shown in FIG. 26. In this state, the hole H6 is exposed to atmospheric pressure, and air is applied through the hole H2. As a result, the diluent 40 flows into the measurement flow path 44c and the first overflow path 44Ad.

When the fact that the diluent 40 has reached the first overflow path 44Ad is detected, the holes H2, H6 are closed, as shown in FIG. 28. Then, with the hole H9 exposed to atmospheric pressure, air is applied through the hole H4. As a result, a predetermined amount of diluent 40a retained in the measurement flow path 44c flows into the first dilution tank 42A. In the first dilution tank 42A, the blood Sa and the diluent 40a are stirred by e.g. rotating a stirrer (not shown). As a result, the first blood sample DS1 is obtained as shown in FIG. 29.

Then, as shown in FIG. 29, with the hole H10 exposed to atmospheric pressure, air is applied through the hole H9. As a result, the first blood sample DS1 flows from the first dilution tank 42A into the overflow path 45d through the introduction flow path 45a.

When the fact that the first blood sample DS1 has flown into the overflow path 45d is detected, the second dilution tank 42B is exposed to atmospheric pressure, as shown in FIG. 30. This step is performed by exposing the hole H12 shown in FIG. 26 to atmospheric pressure. As a result, as shown in FIG. 30, the first blood sample DS1 retained in the first dilution tank 42A flows also into the measurement flow path 45c in addition to the overflow path 45d. An orifice 45e is provided on the downstream side of the measurement flow path 45c. Thus, when the first blood sample DS1 reaches the orifice 45e, a large pressure loss occurs. The pressure loss prevents the first blood sample DS1 from flowing to the downstream side of the orifice 45e. The cross sectional area of the overflow path 45d is larger than that of the orifice 45e. Thus, the first blood sample DS1 flows selectively into the overflow path 45d. When the application of air through the hole H9 is continued, all the first blood sample 42B flows out of the first dilution tank 42A, and the introduction flow path 45a and the upstream portion of the overflow path 45d are filled with air. In this state, a predetermined amount of first blood sample DS1a is separated and retained in the measurement flow path 45c.

When the fact that the upstream portion of the overflow path 45d is filled with air is detected, the hole 10 is closed, as shown in FIG. 31. Further, the hole H12 shown in FIG. 26 is also closed, and the application of air through the hole H9 is stopped. Then, as shown in FIG. 31, with the hole H7 exposed to atmospheric pressure, air is applied through the hole H2. As a result, the diluent 40 flows from the diluent tank 41 into the measurement flow path 44c and the second overflow path 44Bd.

In the process steps shown in FIGS. 29 and 30, a small amount of first blood sample DS1 may unduly flow from the first dilution tank 42A into the second overflow path 44Bd. However, in the process step shown in FIG. 31, the diluent 40 pushes such a small amount of first blood sample DS1 toward a deeper portion of the overflow path 44Bd. Thus, the dilution ratio is prevented from becoming inaccurate due to the small amount of first blood sample DS1.

When the fact that the diluent 40 has flown into the second overflow path 44Bd is detected, the holes H2 and H7 are closed, as shown in FIG. 32. Then, with the hole H12 shown in FIG. 26 exposed to atmospheric pressure, air is applied through the opening H4, as shown in FIG. 32. As a result, the diluent 40 flows from the measurement flow path 44c into the second dilution tank 42B through the measurement flow path 45c. In this process, the first blood sample DS1a retained in the measurement flow path 45c is pushed into the second dilution tank 42B together with the diluent 40. As a result, second blood sample DS2 obtained by mixing the first blood sample DS1a and the diluent 40 is retained in the second dilution tank 42B.

In this embodiment, the two-stage dilution for preparing the first and the second blood samples DS1 and DS2 is achieved by the structure including only a single diluent tank 41 for storing the diluent 40 as the dilution medium. With this structure, the size of the cartridge A2 and the cost for manufacturing the cartridge A2 are reduced. Moreover, since the first and the second overflow paths 44Ad and 44Bd are provided, the diluent 40 is not discharged from the cartridge A2 even when the two-stage dilution is performed.

FIG. 33 shows an analyzer cartridge according to a third embodiment of the present invention. The cartridge A3 according to this embodiment differs from the foregoing embodiments in that the cartridge does not incorporate diluent. The analysis process by the first through the fourth analysis portions 5A, 5B, 5C and 5D are performed in the same manner as in the foregoing embodiments.

In this embodiment, the hole H2 is connected to the first dilution tank 42A, whereas the hole H3 is connected to the second dilution tank 42B. The dilution process using the cartridge A3 will be described below.

First, as shown in FIG. 34, blood S is introduced from the hole H1. Then, the blood S is caused to flow into the introduction flow path 43a by holding the holes H2, H8 side in a low-pressure state while holding the hole H1 side in a high-pressure state. In this step, the holes other than the holes H1, H2 and H8, i.e., the holes H3, H10, H14 and H15 may be either opened or closed. By keeping the high-pressure state of the hole H1, a predetermined amount of blood Sa is separated and retained in the measurement flow path 43c.

Then, as shown in FIG. 35, diluent 40Aa is injected into the first dilution tank 42A. Specifically, a predetermined amount of diluent 40Aa is injected from the hole H2. Alternatively, solute of the diluent 40Aa in a dry state may be applied in advance in the first dilution tank 42A, and a predetermined amount of distilled water may be injected from the hole H2 into the first dilution tank to mix with the solute to prepare the diluent 40Aa.

Then, by holding the hole H1 side in a high-pressure state, the blood Sa is fed from the measurement flow path 43c into the first dilution tank 42A. The feeding of the blood Sa is performed while stirring the diluent 40Aa in the first dilution tank 42A. Due to the stirring, on flowing into the first dilution tank 42A, the blood Sa is mixed with the diluent 40Aa. As a result, as shown in FIG. 36, the first blood sample DS1 is obtained. Thus, the first dilution step is completed. The first blood sample DS1 is used for the measurement of CRP by the fourth analysis portion 5D. Further, the first blood sample DS1 is used for the counting of white blood cells in the first analysis portion 5A and the measurement of Hb in the third analysis portion 5C after the hemolytic treatment in the buffer tank 46.

The second dilution step will be described below. First, as shown in FIG. 37, the hole H2 side is held in a high-pressure state, whereas the holes H3, H10 side is held in a low-pressure state. By continuing this state, part of the first blood sample DS1 retained in the first dilution tank 42A is caused to flow into the measurement flow path 45c and retained in the flow path as the first blood sample DS1a.

Then, as shown in FIG. 38, the diluent 40Ba is injected into the second dilution tank 42B. Specifically, a predetermined amount of diluent 40Ba is injected from the hole H3. Alternatively, solute of the diluent 40Ba in a dry state may be applied in advance in the second dilution tank 42B, and a predetermined amount of distilled water may be injected from the hole H3 into the second dilution tank to mix with the solute to prepare the diluent 40Ba.

Then, by holding the hole H2 side in a high-pressure state, the first blood sample DS1a is fed from the measurement flow path 45c into the second dilution tank 42B. The feeding of the first blood sample DS1a is performed while stirring the diluent 40Ba in the second dilution tank 42B. By the stirring, on flowing into the second dilution tank 42B, the first blood sample DS1a is mixed with the diluent 40Ba. As a result, as shown in FIG. 39, the second blood sample DS2 is obtained. Thus, the second dilution step is completed. The second blood sample DS2 is used for the counting of white blood cells in the second analysis portion 5B.

According to this embodiment, the cartridge A3 does not need to incorporate measures to store diluent for a long time. The structure of the cartridge A3 is simple, which leads to a reduction in the cost for manufacturing the cartridge A3.

The liquid feeding method and the cartridge used for the method according to the present invention are not limited to the foregoing embodiments. The specific structure of each part of the liquid feeding method and the cartridge according to the present invention may be varied in many ways.

As the high-pressure state and the low-pressure state in a minute flow path, the low-pressure state may be provided by applying negative pressure instead of exposure to atmospheric pressure, whereas the high-pressure state may be provided by exposure to atmospheric pressure. The pressure in the high-pressure state may be higher than atmospheric pressure, whereas the pressure in the low-pressure state may be lower than atmospheric pressure.

The material of the main body is not limited to a transparent one but may be partially opaque. In this case, at least the portion corresponding to the optical analysis portion is made transparent. Although the use of a printed wiring board is preferable for thickness reduction, a rigid substrate may be used.

The ratio of dilution by the dilution means can be increased by appropriately setting the size of a flow path, for example.

The dilution is not limited to the two-stage dilution. For instance, the dilution may be performed only once or three times or more.

The cartridge according to the present invention is not limited to the use for blood analysis and may be used for the analysis of various kinds of sample liquid. The cartridge according to the present invention may not include an analysis portion and may be designed just to prepare diluted sample liquid for counting blood cells, for example.

Figure 1:
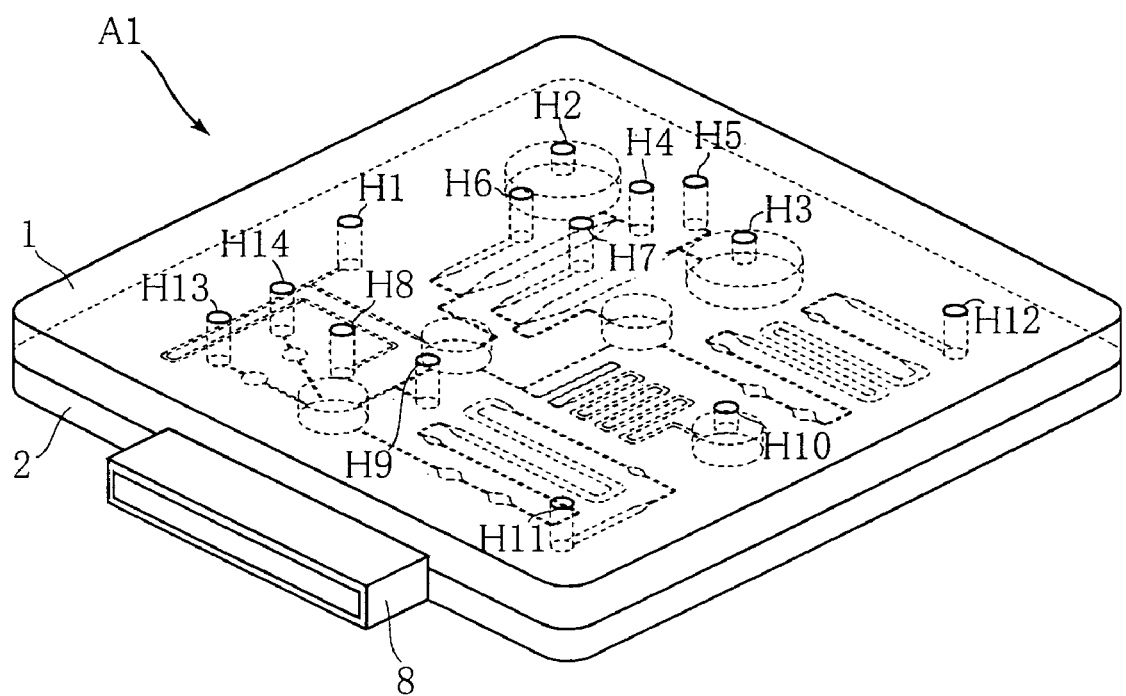
FIG. 1 is an overall perspective view showing a cartridge according to a first embodiment of the present invention.
Figure 2:
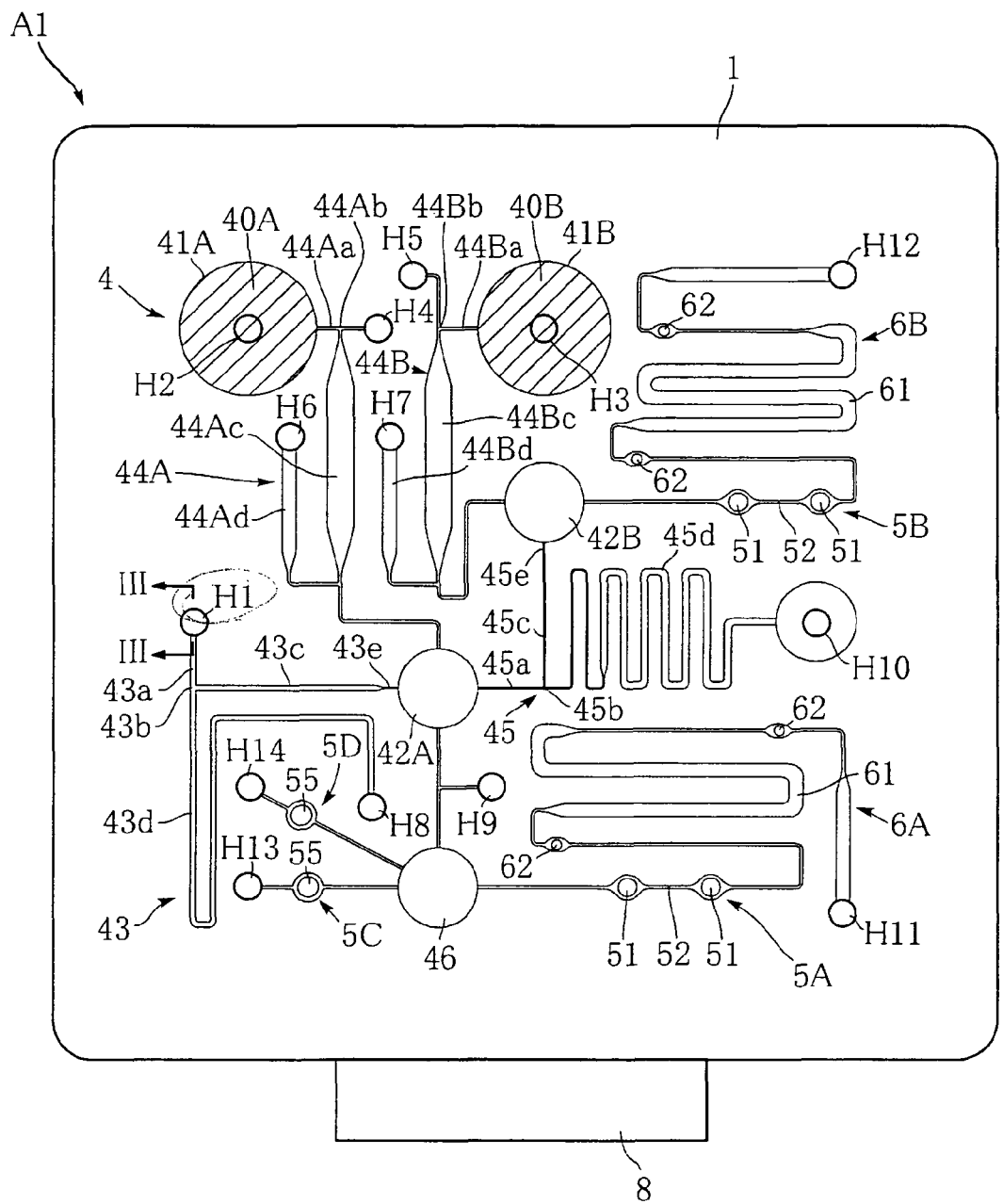
FIG. 2 is a plan view showing the cartridge according to the first embodiment of the present invention.
Figure 3:
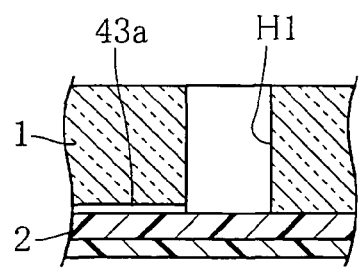
FIG. 3 is a sectional view of a principal portion taken along lines III-III in FIG. 2.
Figure 4:
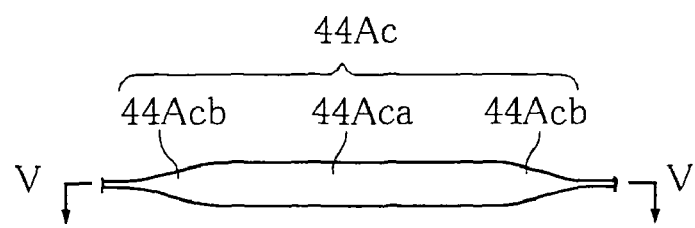
FIG. 4 is a plan view showing a principal portion of a measurement flow path of the cartridge according to the first embodiment of the present invention.
Figure 5:
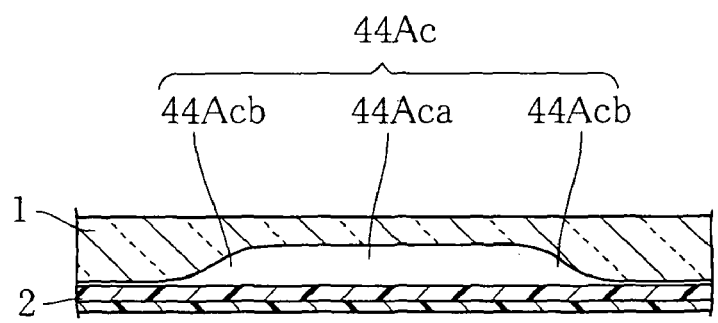
FIG. 5 is a sectional view of a principal portion taken along lines V-V in FIG. 4.
Figure 6:
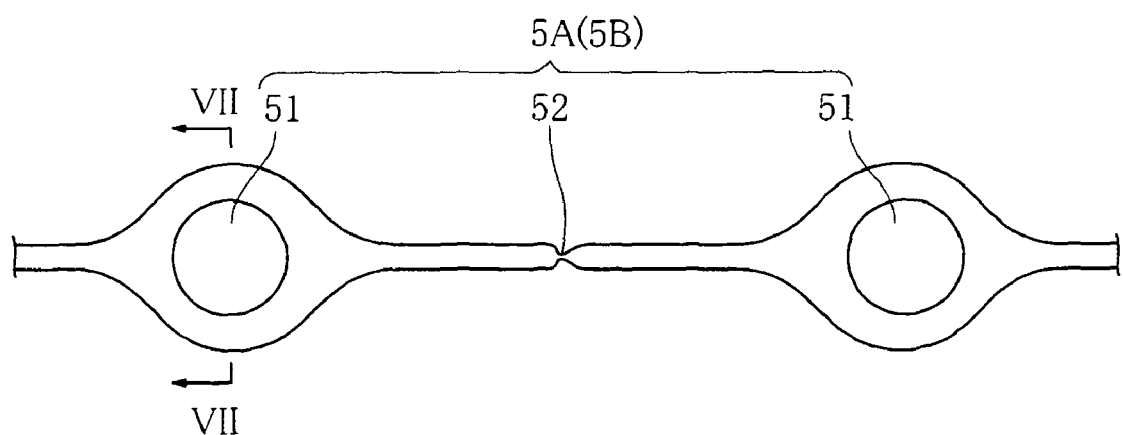
FIG. 6 is a plan view showing a principal portion of a first (second) analysis portion of the cartridge according to the first embodiment of the present invention.
Figure 7:
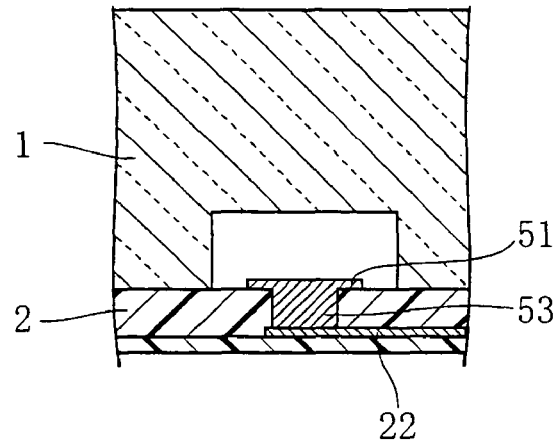
FIG. 7 is a sectional view of a principal portion taken along lines VII-VII in FIG. 6.
Figure 8:
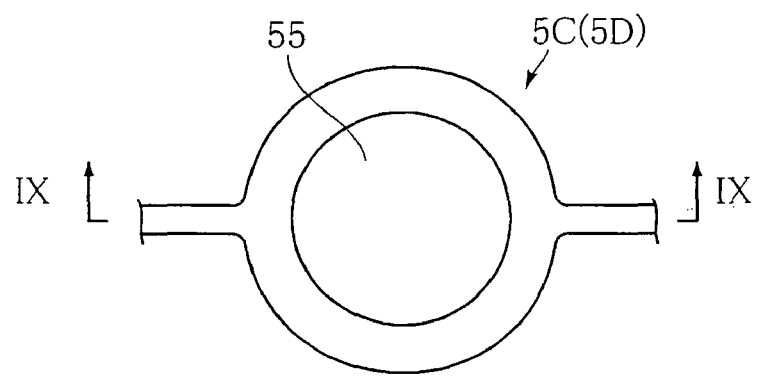
FIG. 8 is a plan view showing a principal portion of a third (fourth) analysis portion of the cartridge according to the first embodiment of the present invention.
Figure 9:
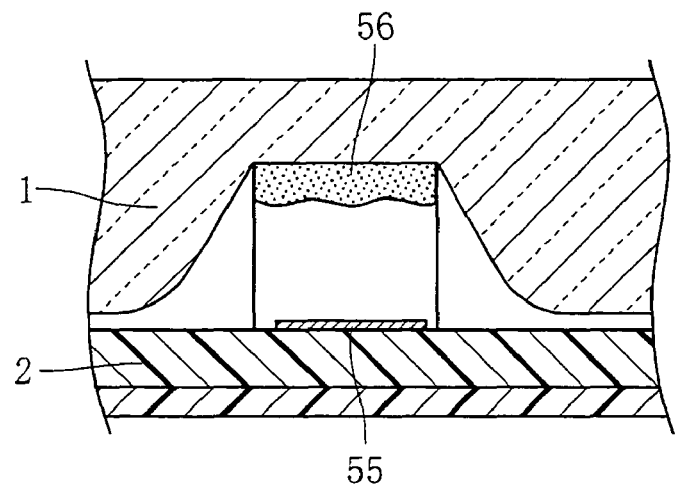
FIG. 9 is a sectional view of a principal portion taken along lines IX-IX in FIG. 8.
Figure 10:
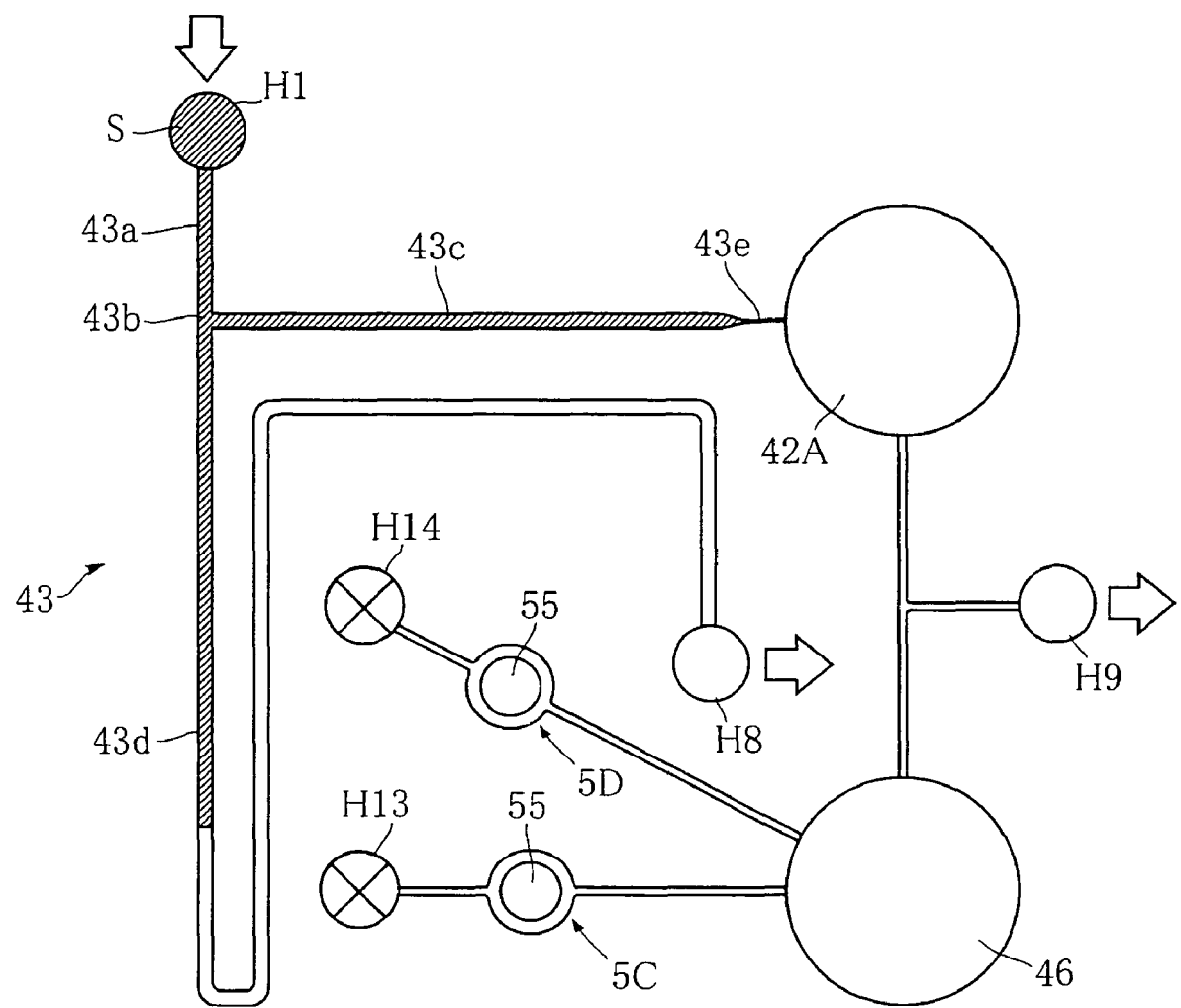
FIG. 10 is a plan view of a principal portion for showing a blood measurement step in a liquid feeding method using the cartridge shown in FIG. 1.
Figure 11:
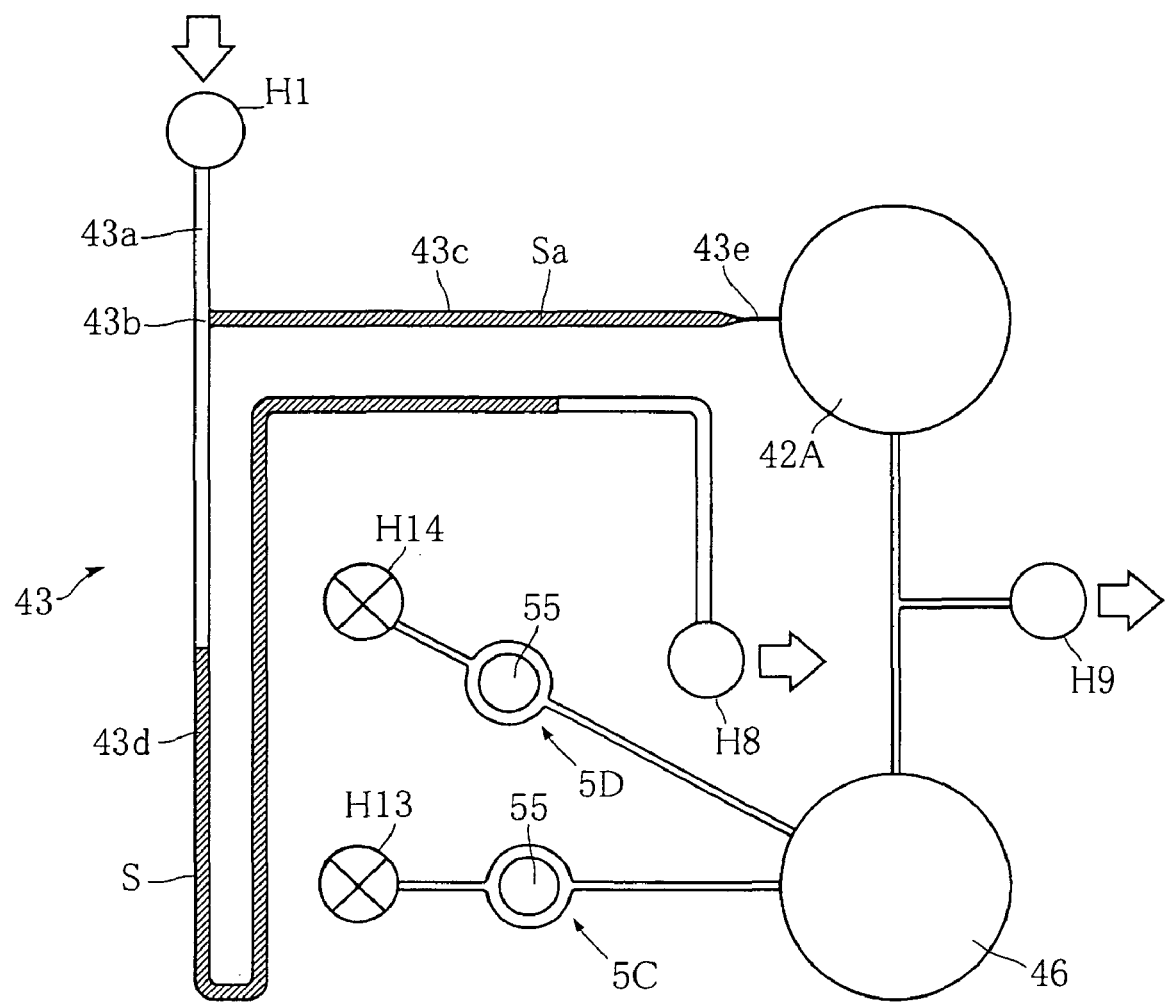
FIG. 11 is a plan view of a principal portion for showing the blood measurement step in the liquid feeding method using the cartridge shown in FIG. 1.
Figure 12:
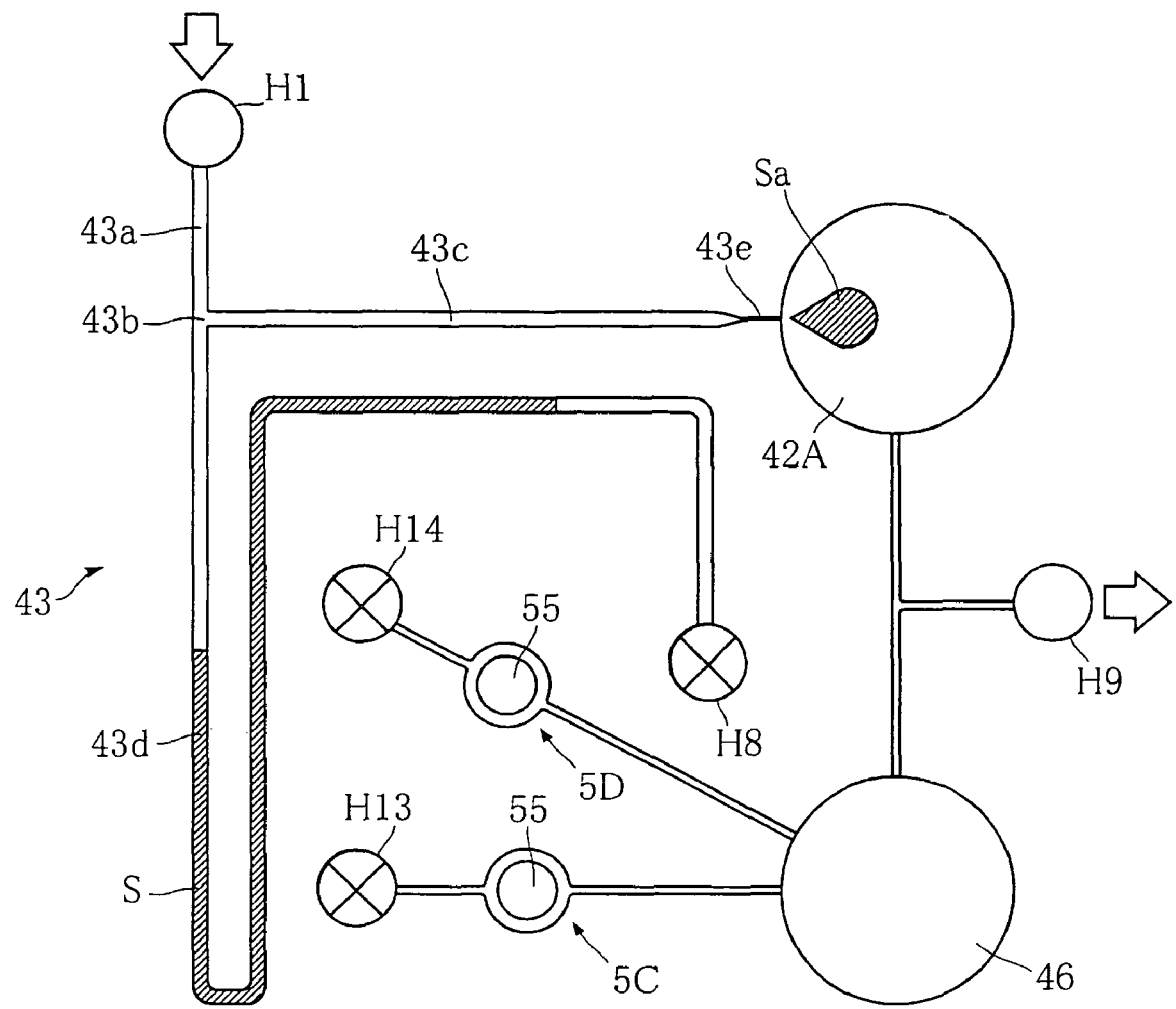
FIG. 12 is a plan view of a principal portion for showing the blood measurement step in the liquid feeding method using the cartridge shown in FIG. 1.
Figure 13:
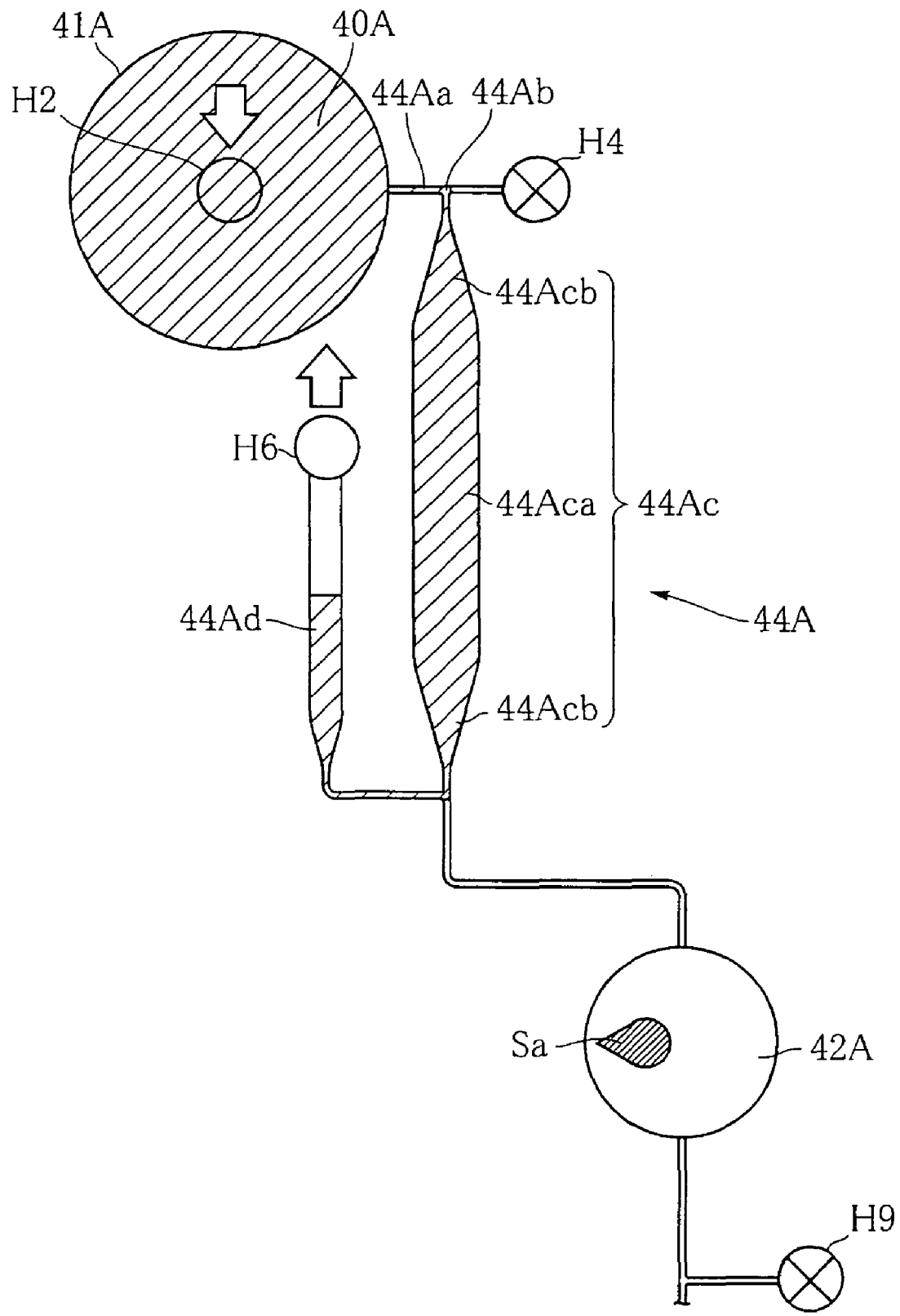
FIG. 13 is a plan view of a principal portion for showing a first dilution step in the liquid feeding method using the cartridge shown in FIG. 1.
Figure 14:
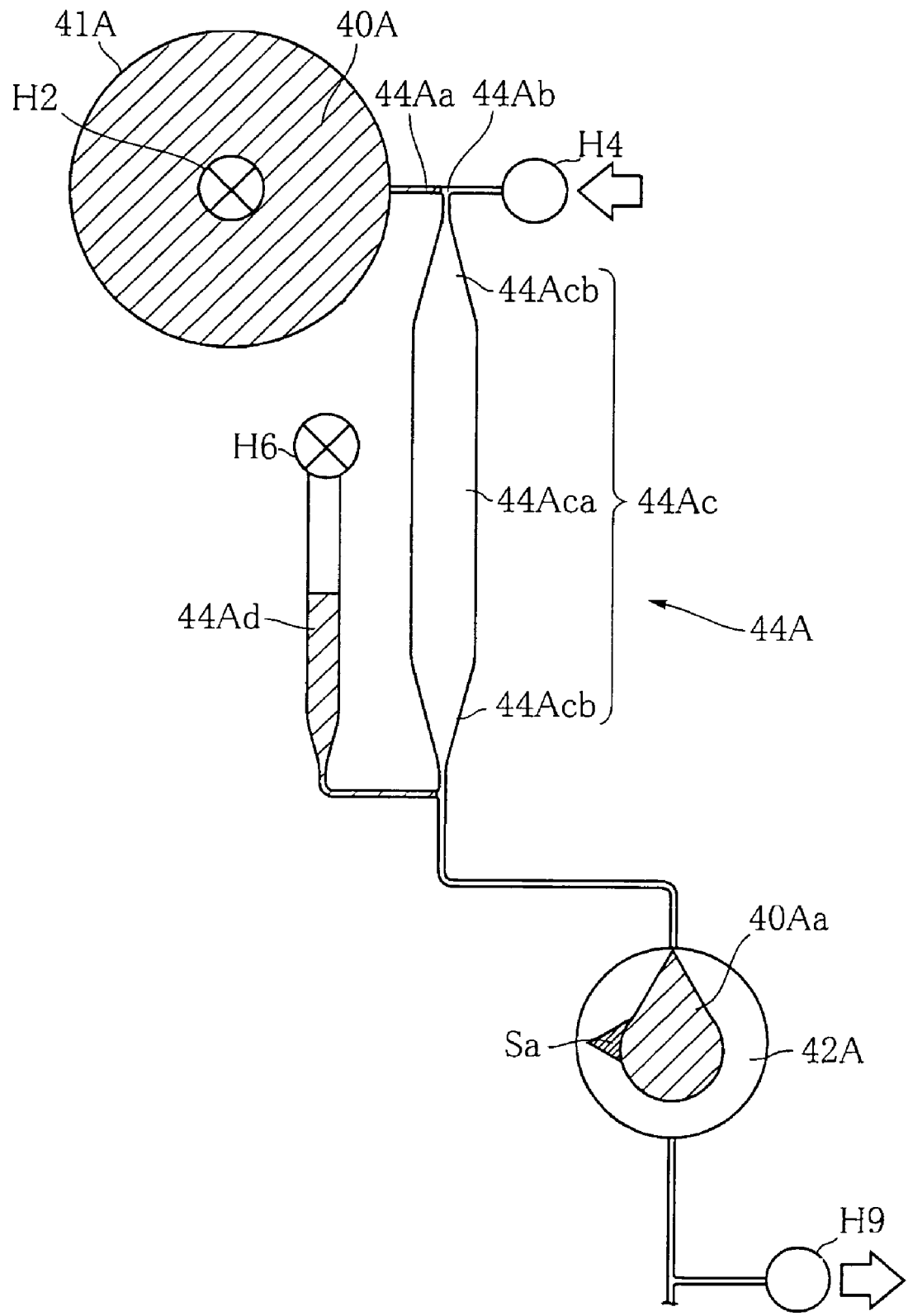
FIG. 14 is a plan view of a principal portion for showing the first dilution step in the liquid feeding method using the cartridge shown in FIG. 1.
Figure 15:
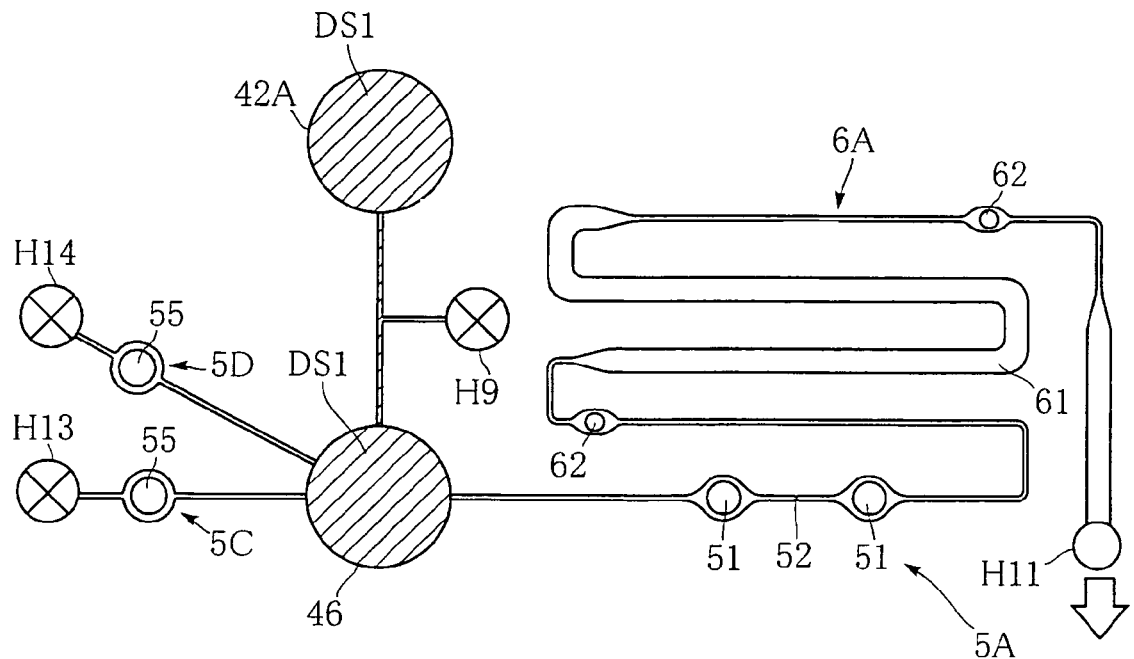
FIG. 15 is a plan view of a principal portion for showing an analysis step by a first analysis portion in the liquid feeding method using the cartridge shown in FIG. 1.
Figure 16:
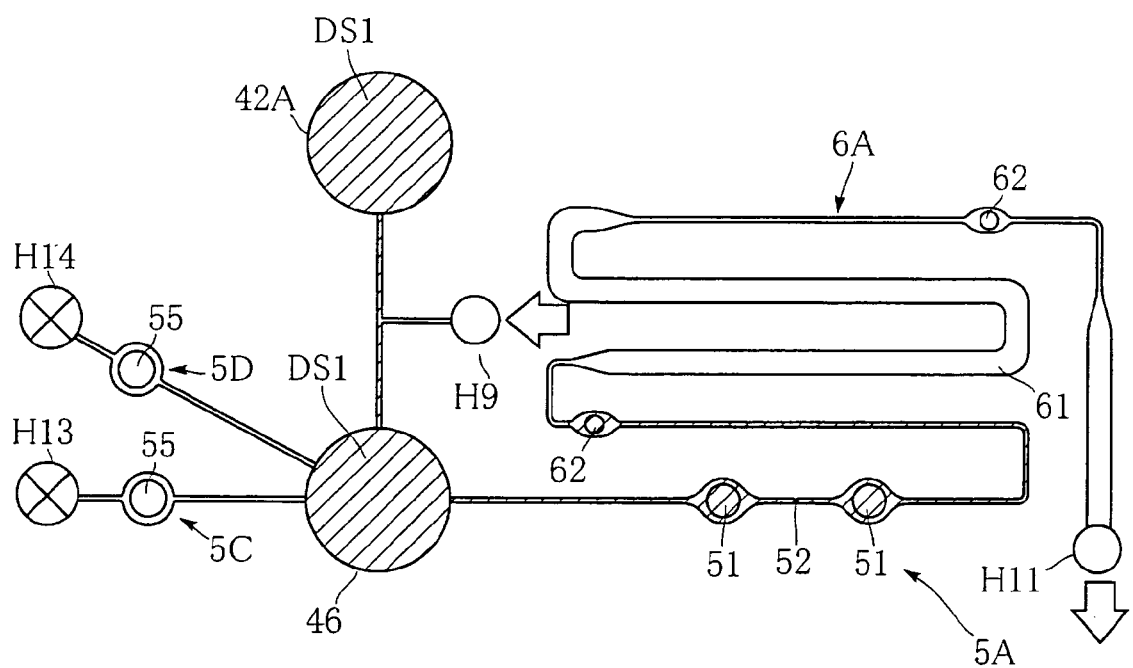
FIG. 16 is a plan view of a principal portion for showing the analysis step by the first analysis portion in the liquid feeding method using the cartridge shown in FIG. 1.
Figure 17:
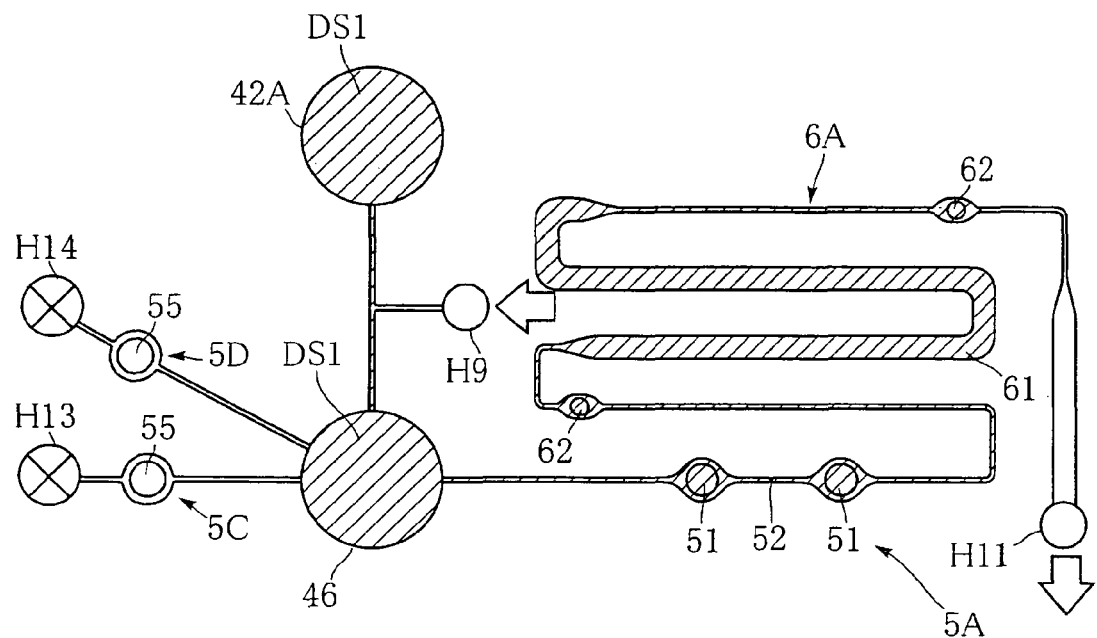
FIG. 17 is a plan view of a principal portion for showing the analysis step by the first analysis portion in the liquid feeding method using the cartridge shown in FIG. 1.
Figure 18:
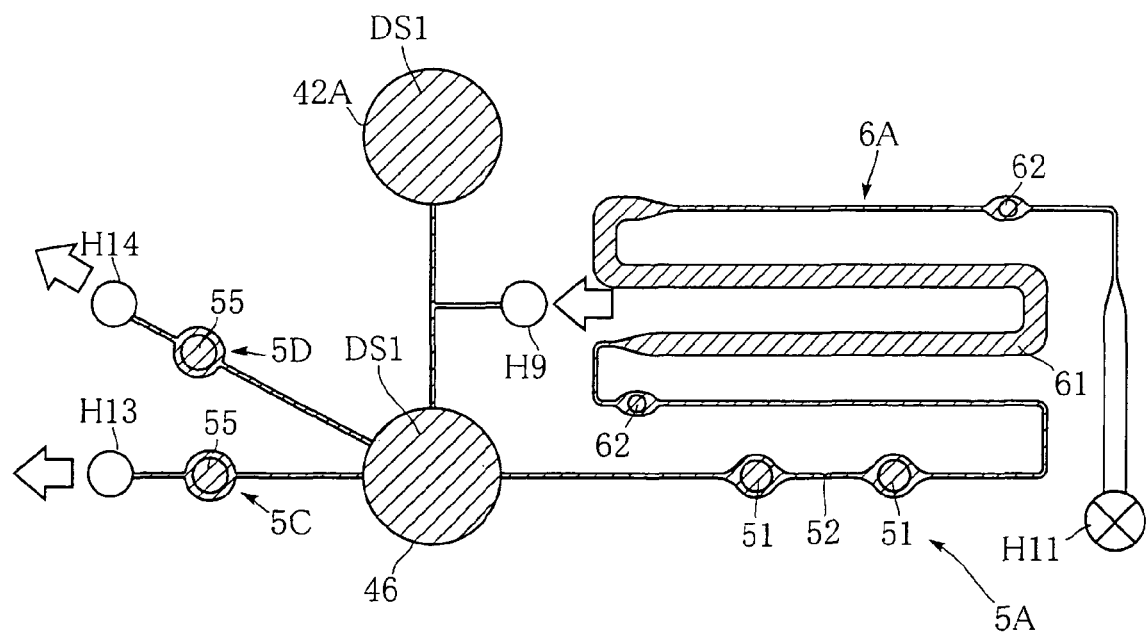
FIG. 18 is a plan view of a principal portion for showing an analysis step by a third and a fourth analysis portions in the liquid feeding method using the cartridge shown in FIG. 1.
Figure 19:
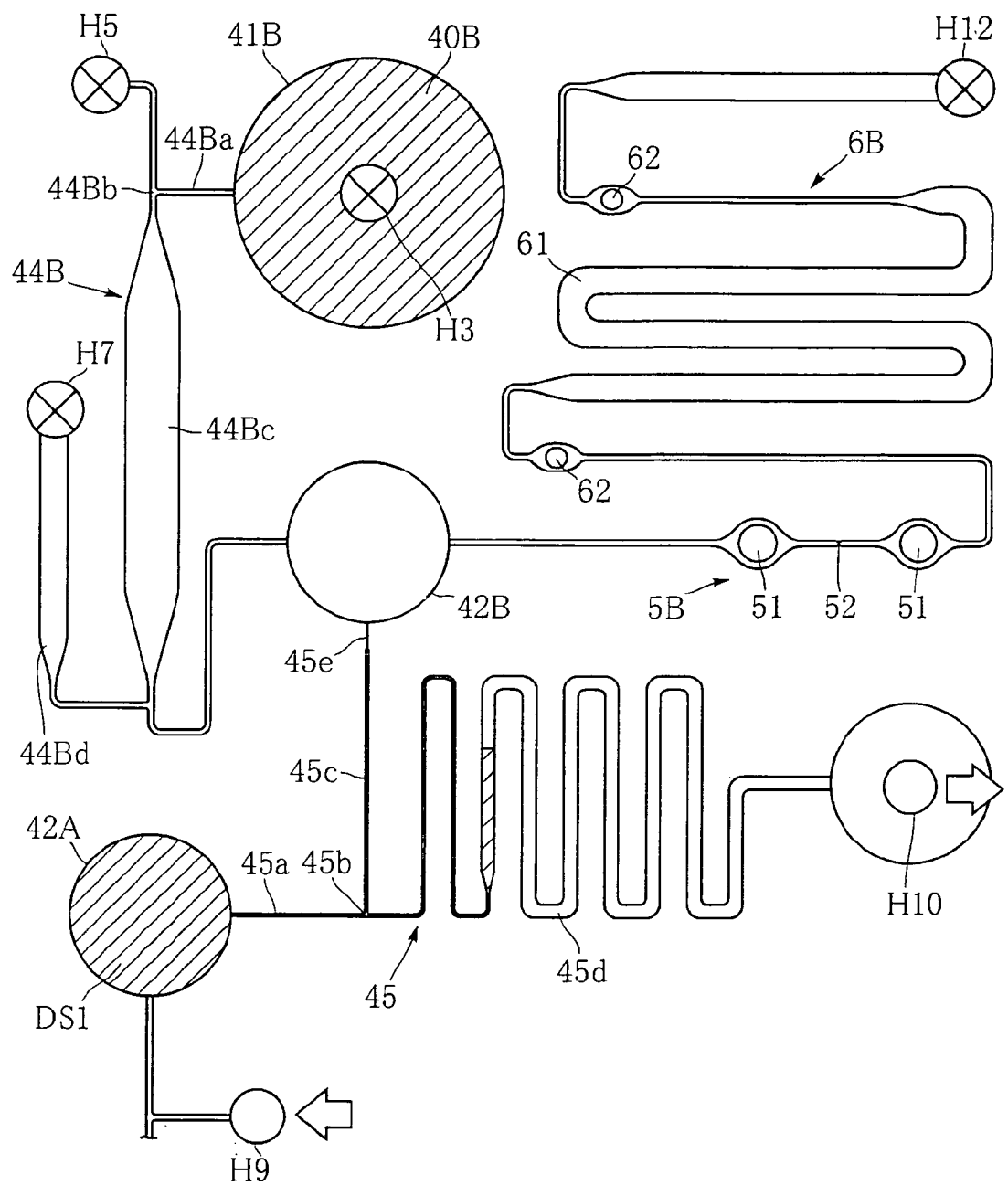
FIG. 19 is a plan view of a principal portion for showing a second dilution step in the liquid feeding method using the cartridge shown in FIG. 1.
Figure 20:
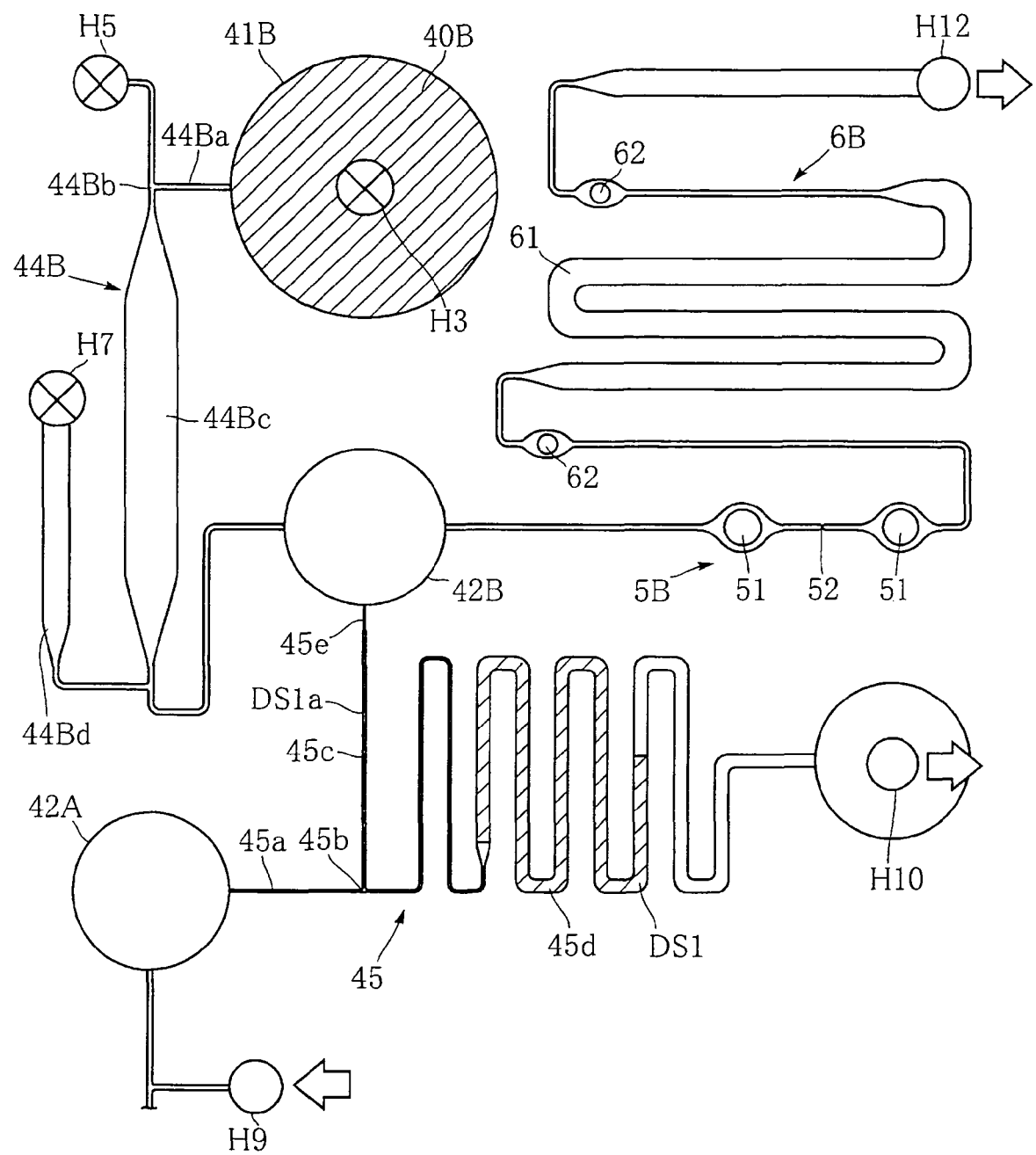
FIG. 20 is a plan view of a principal portion for showing the second dilution step in the liquid feeding method using the cartridge shown in FIG. 1.
Figure 21:
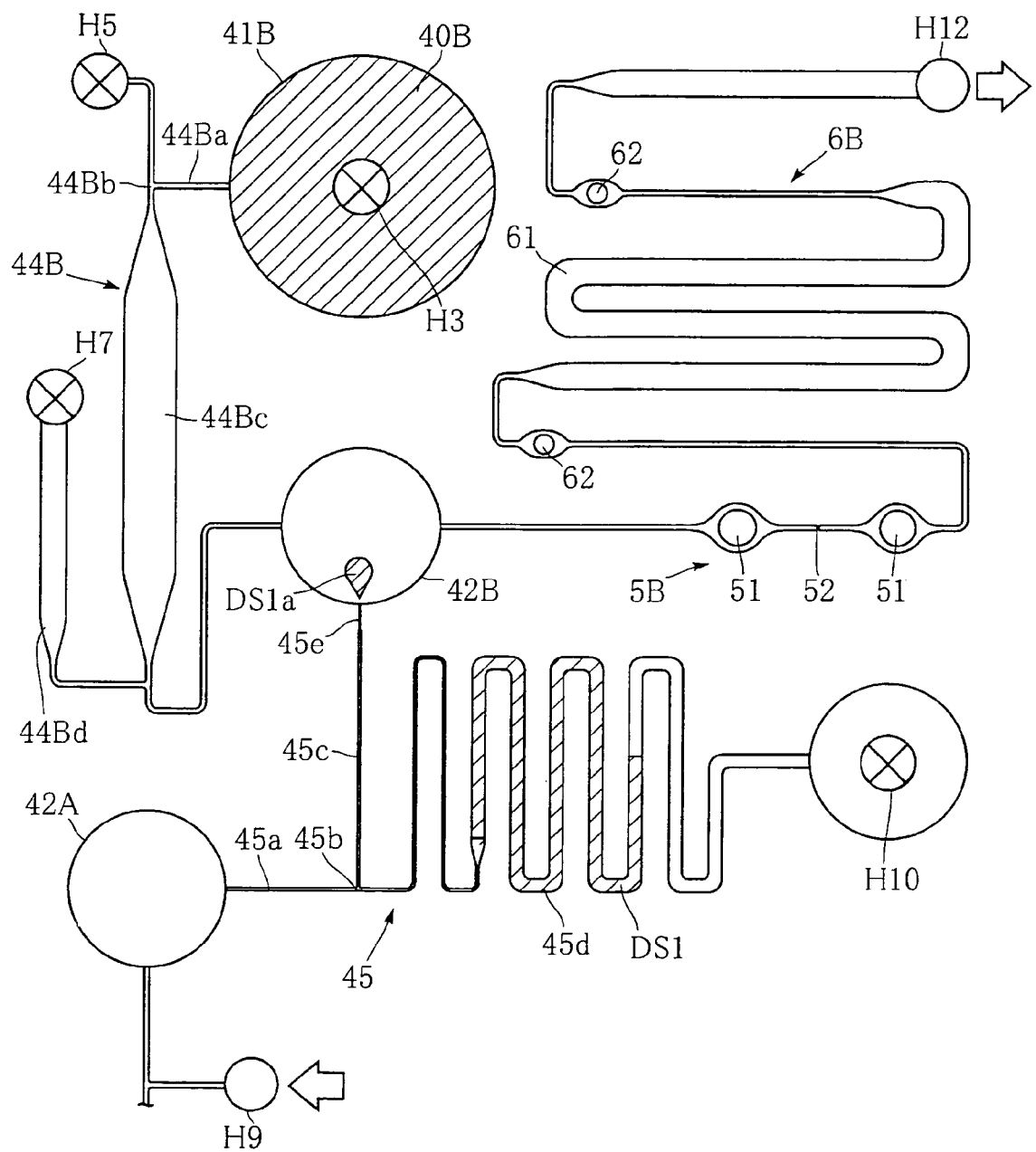
FIG. 21 is a plan view of a principal portion for showing the second dilution step in the liquid feeding method using the cartridge shown in FIG. 1.
Figure 22:
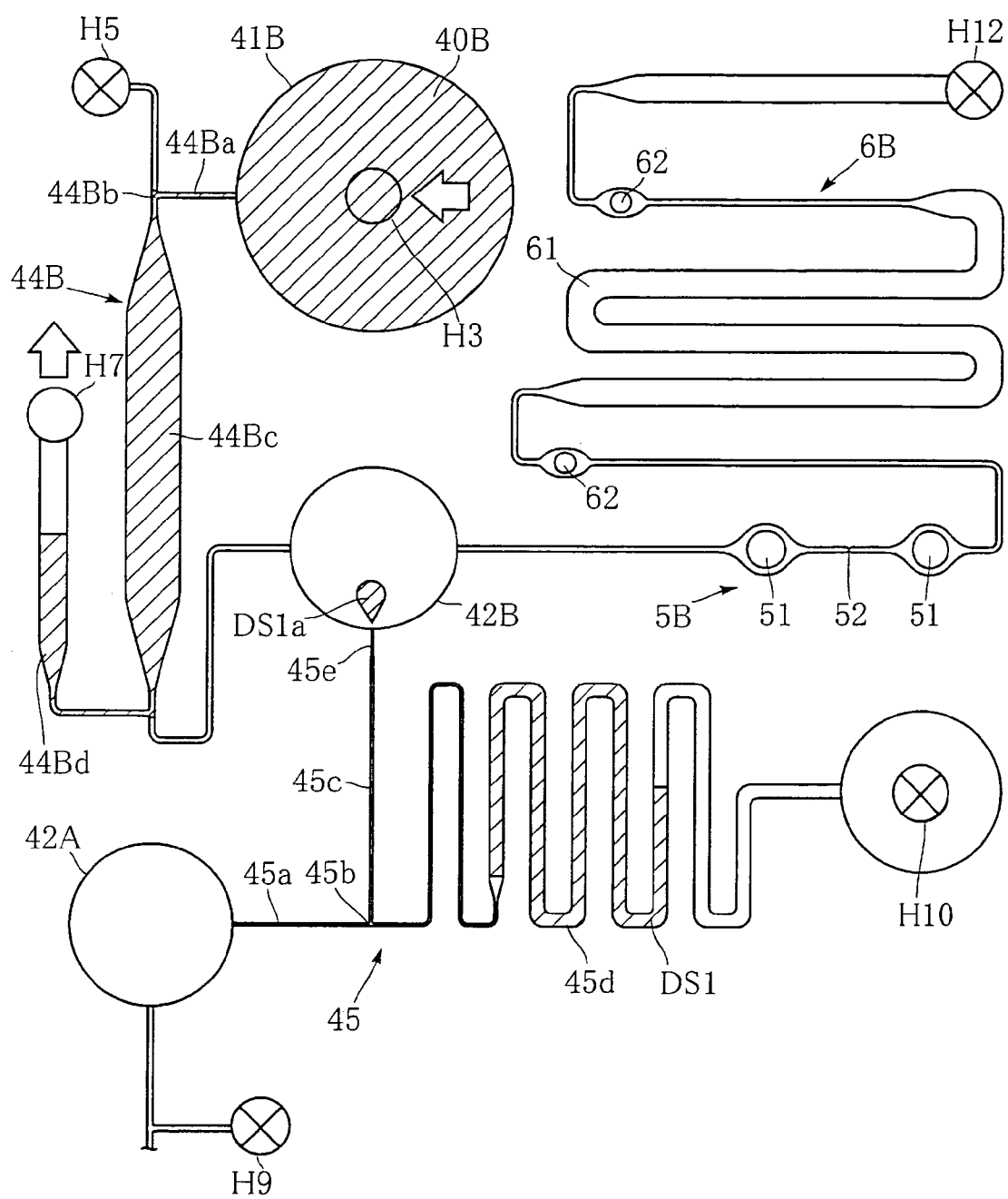
FIG. 22 is a plan view of a principal portion for showing the second dilution step in the liquid feeding method using the cartridge shown in FIG. 1.
Figure 23:
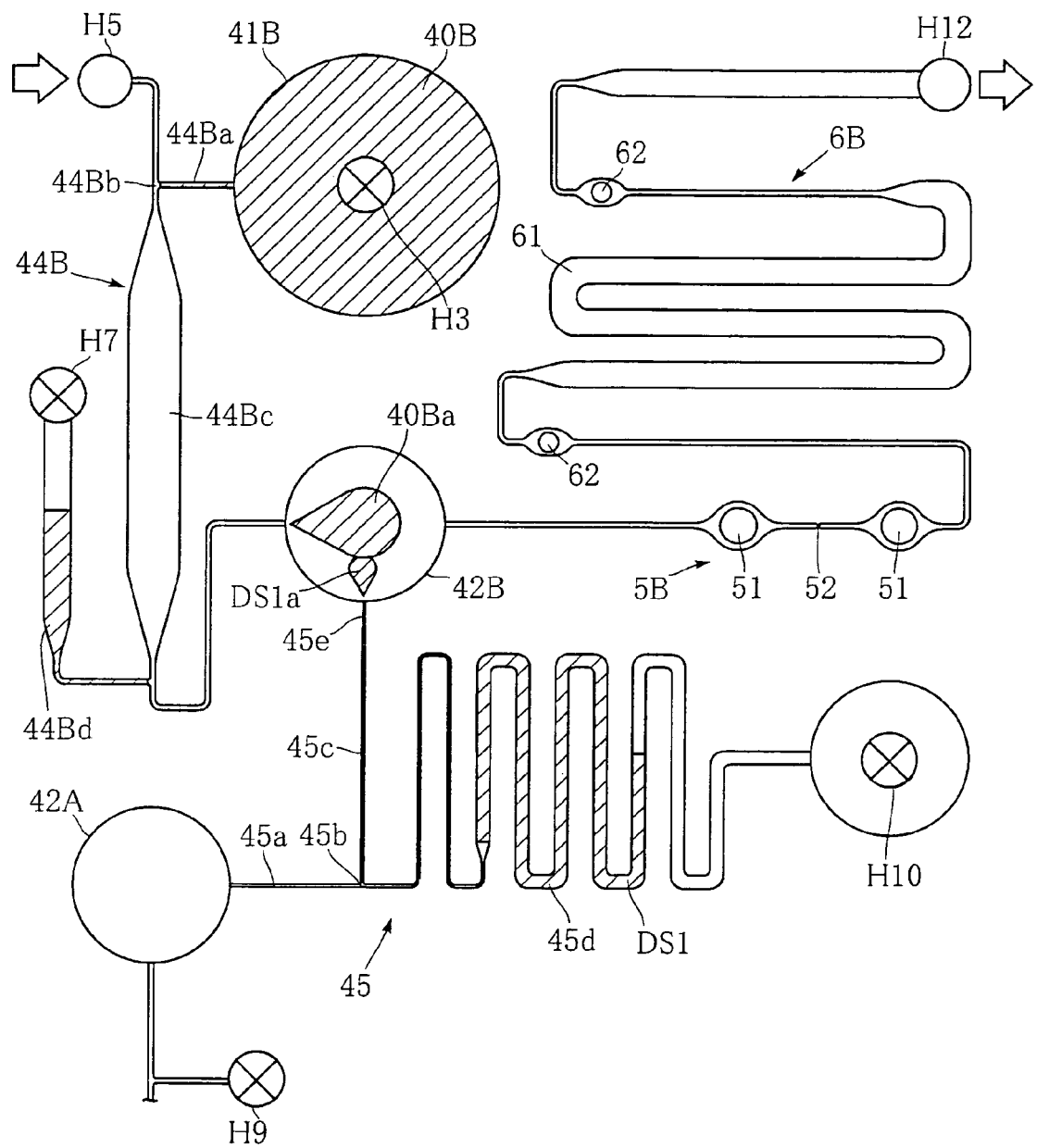
FIG. 23 is a plan view of a principal portion for showing the second dilution step in the liquid feeding method using the cartridge shown in FIG. 1.
Figure 24:
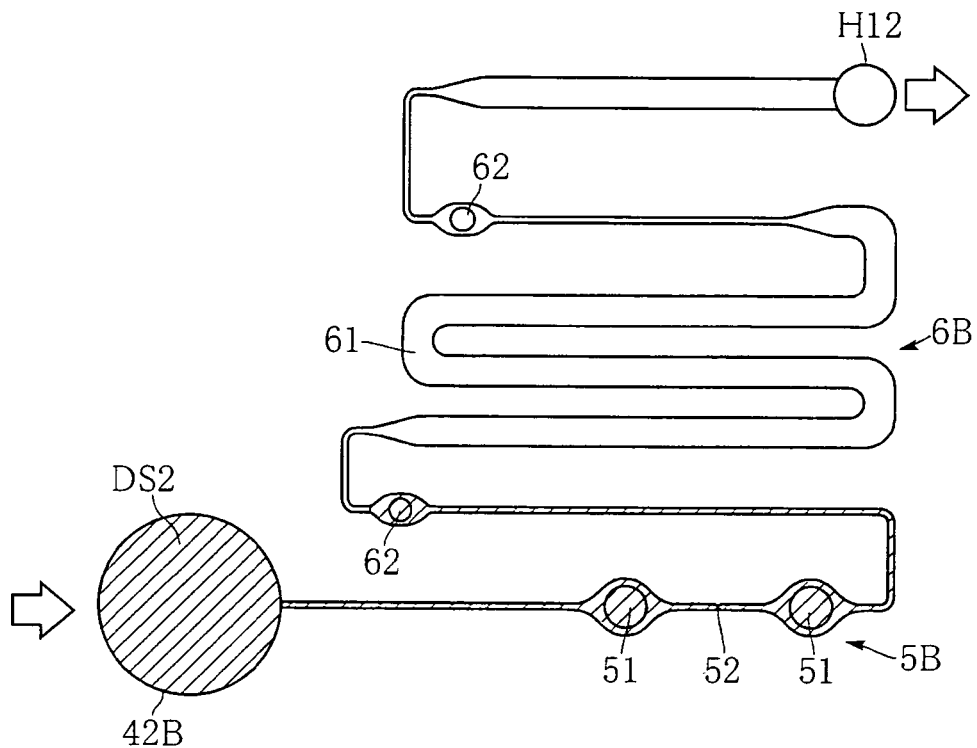
FIG. 24 is a plan view of a principal portion for showing an analysis step by a second analysis portion in the liquid feeding method using the cartridge shown in FIG. 1.
Figure 25:
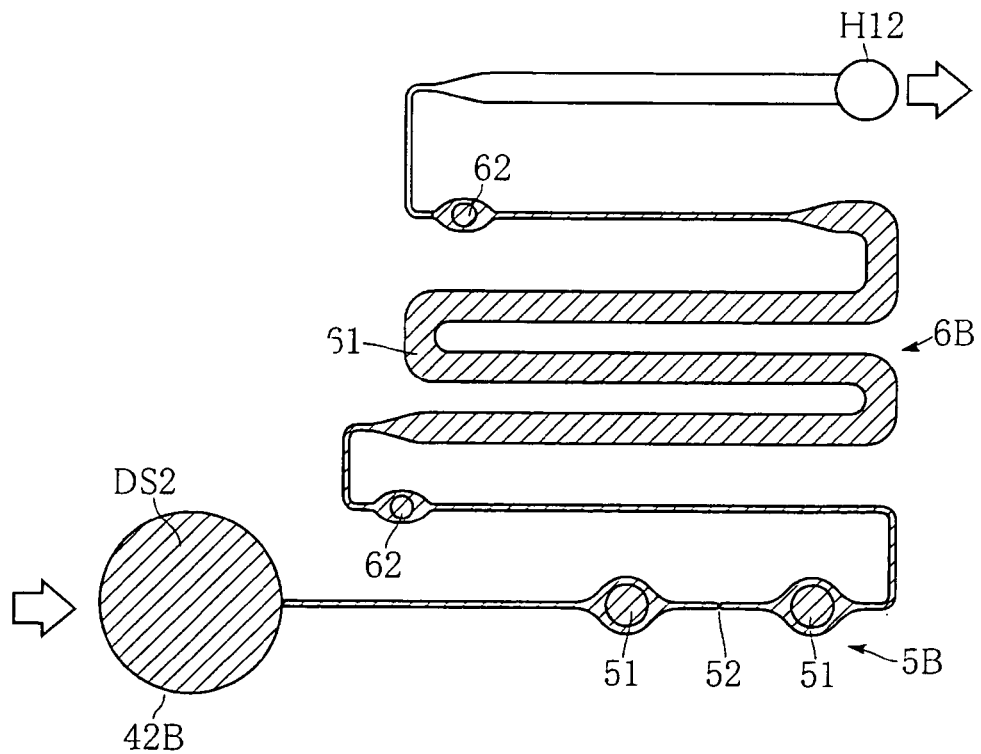
FIG. 25 is a plan view of a principal portion for showing the analysis step by the second analysis portion in the liquid feeding method using the cartridge shown in FIG. 1.
Figure 26:
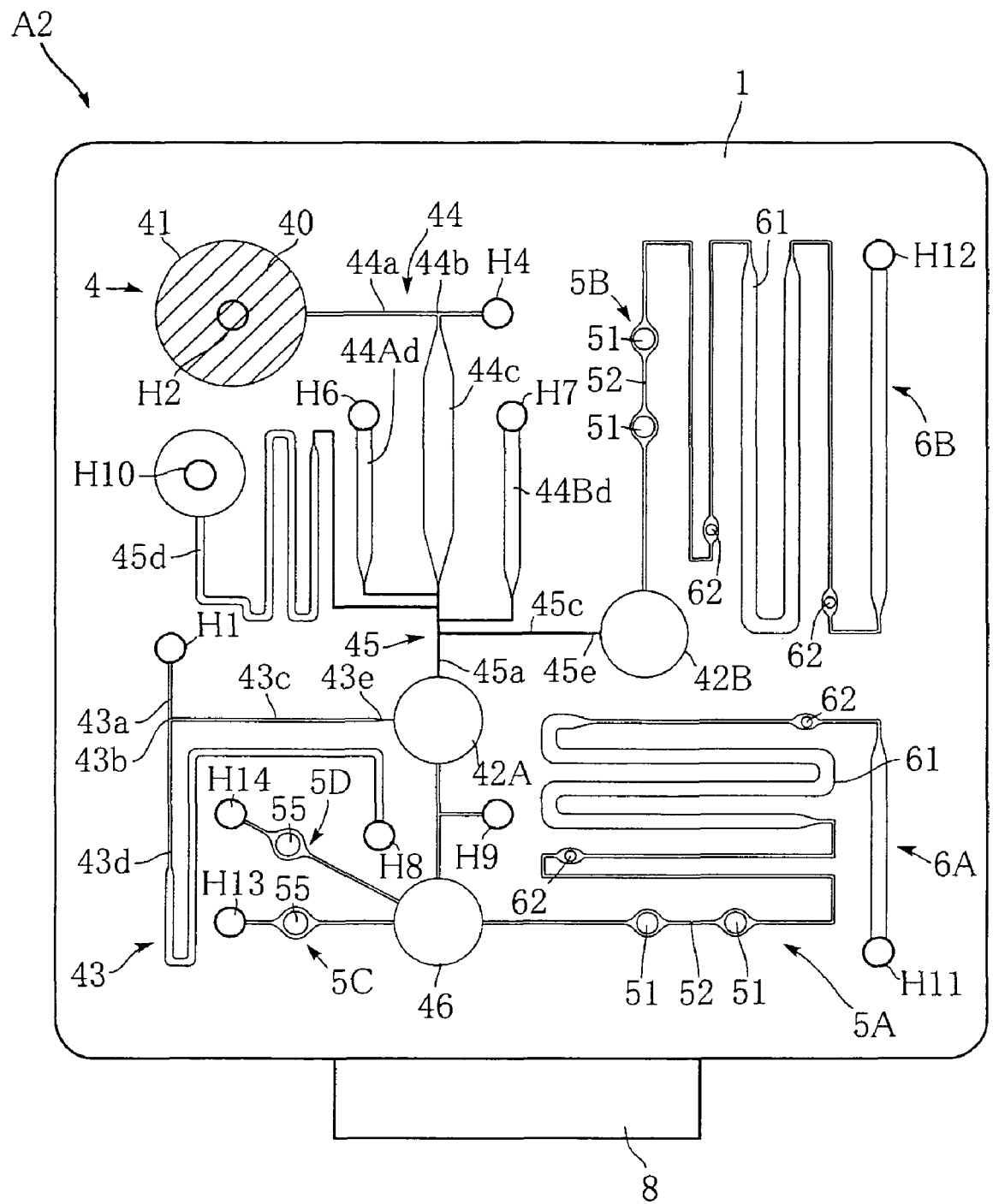
FIG. 26 is a plan view showing a cartridge according to a second embodiment of the present invention.
Figure 27:
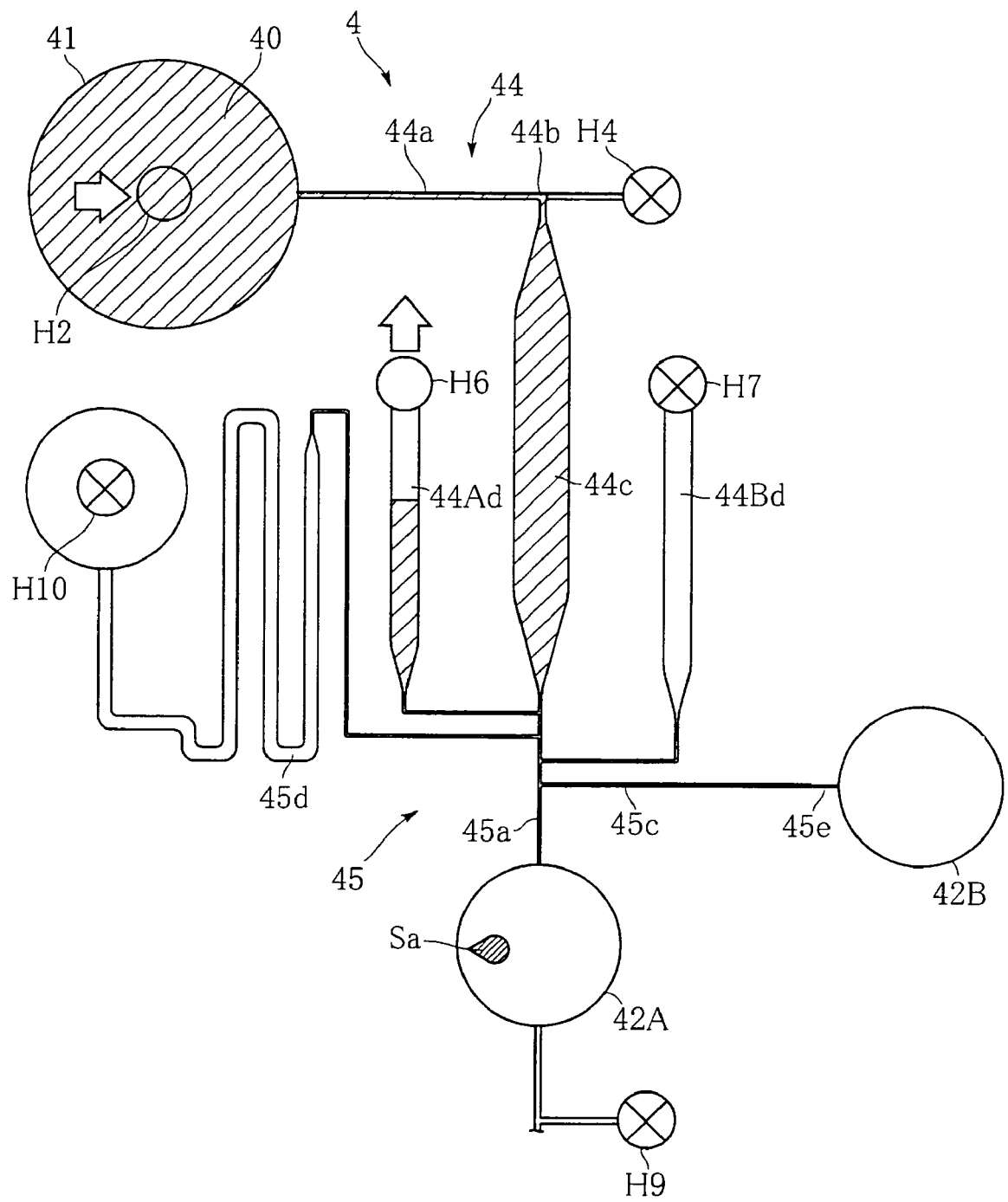
FIG. 27 is a plan view of a principal portion for showing a first dilution step in a liquid feeding method using the cartridge shown in FIG. 26.
Figure 28:
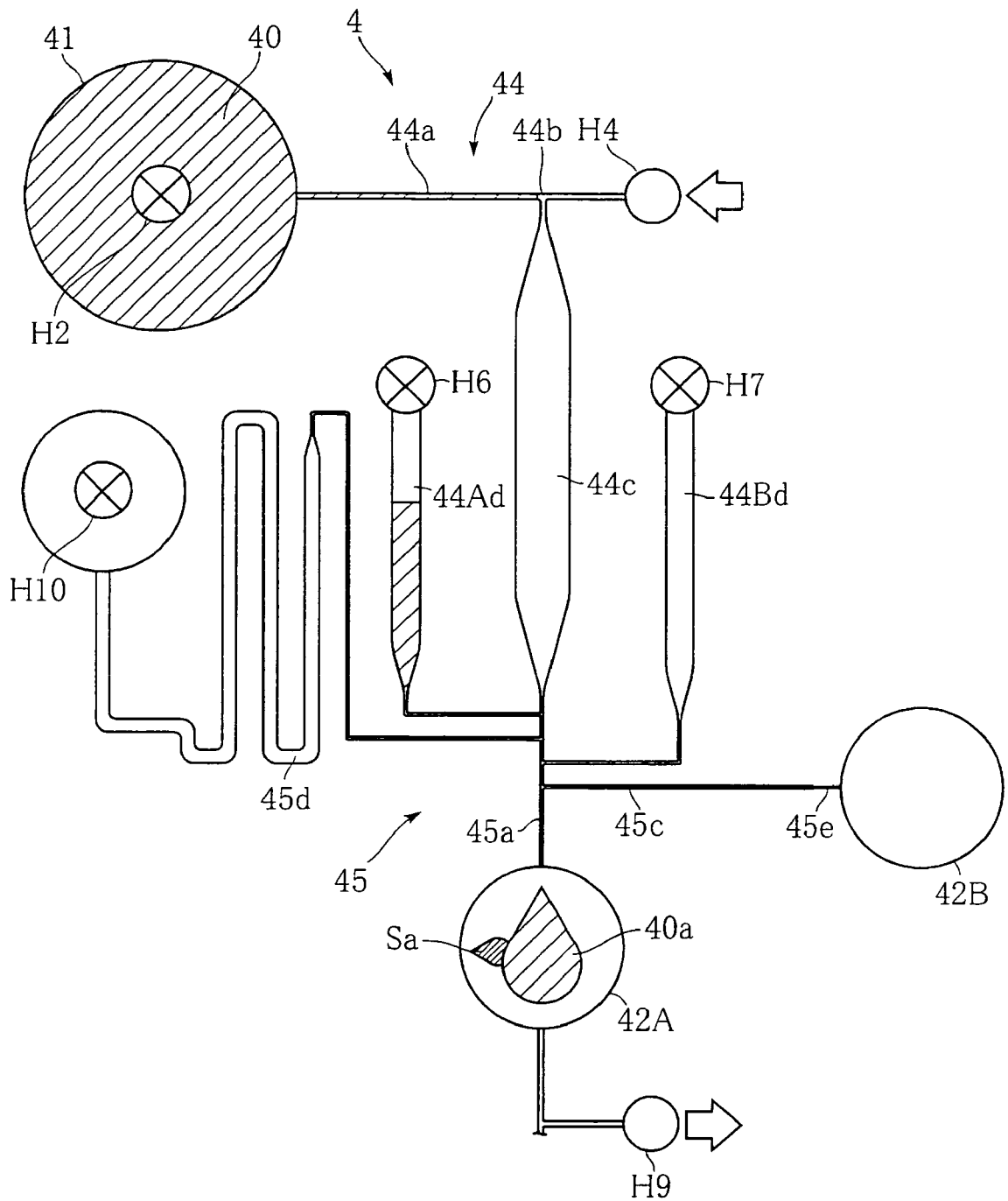
FIG. 28 is a plan view of a principal portion for showing the first dilution step in the liquid feeding method using the cartridge shown in FIG. 26.
Figure 29:
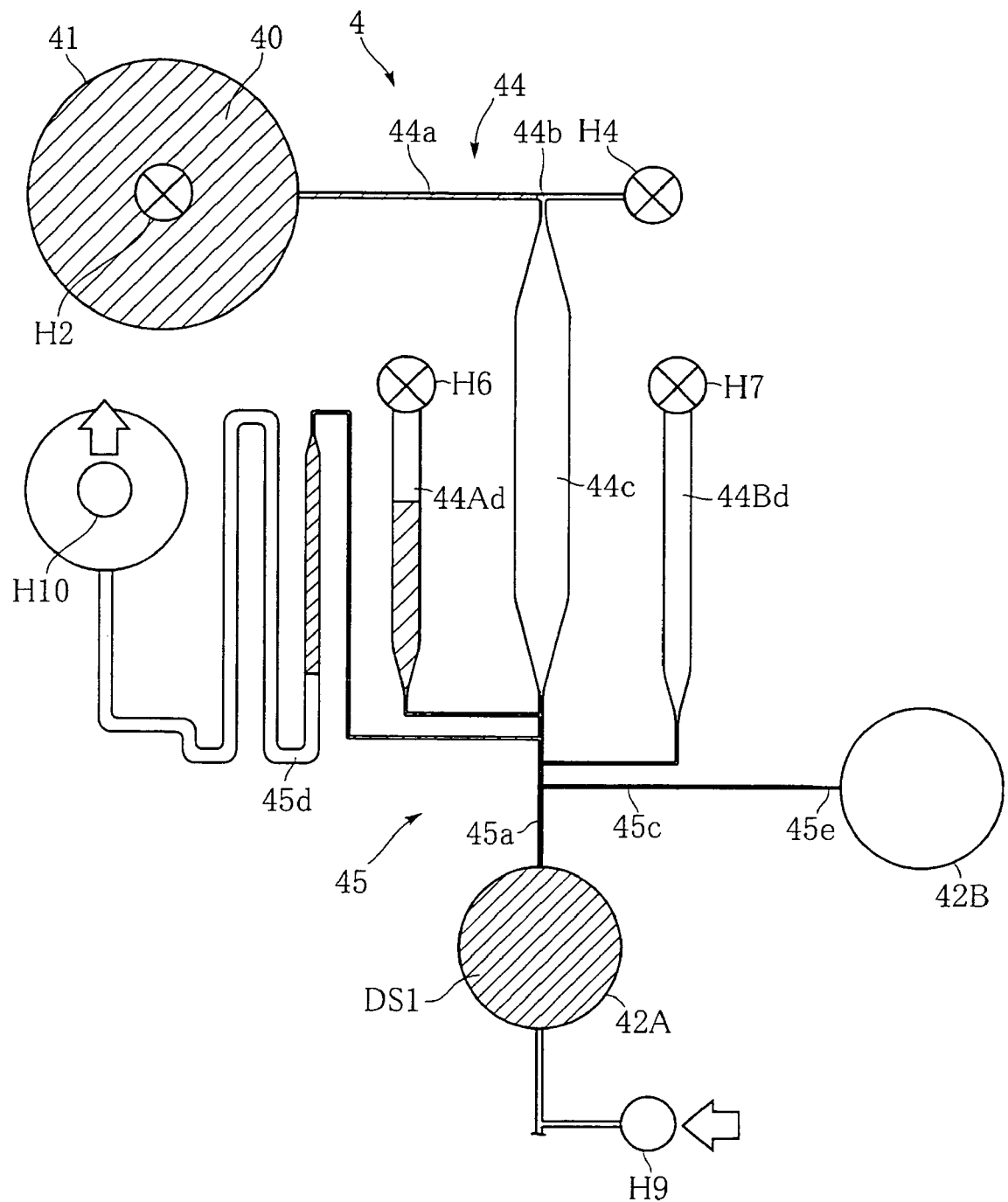
FIG. 29 is a plan view of a principal portion for showing a second dilution step in the liquid feeding method using the cartridge shown in FIG. 26.
Figure 30:
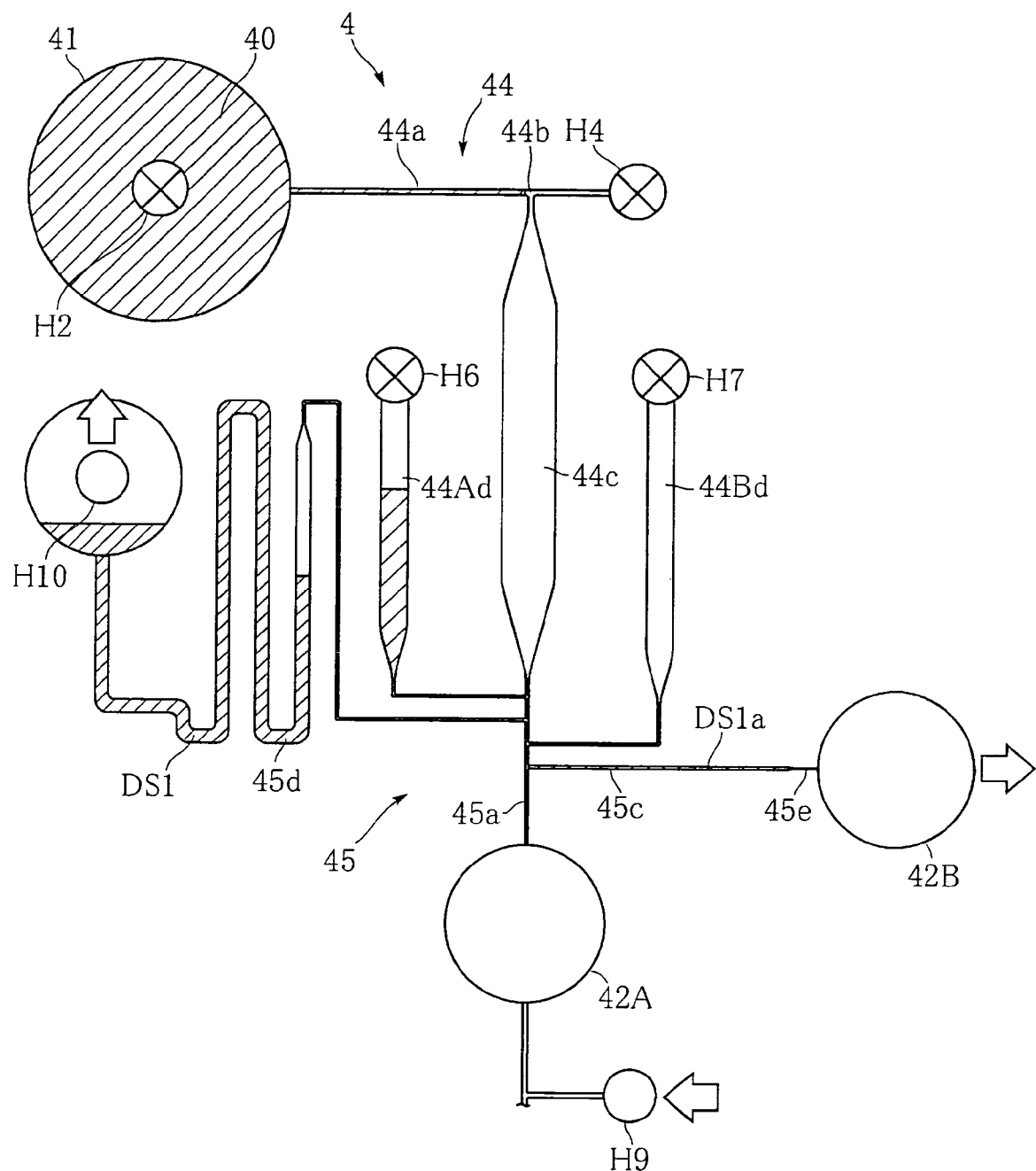
FIG. 30 is a plan view of a principal portion for showing the second dilution step in the liquid feeding method using the cartridge shown in FIG. 26.
Figure 31:
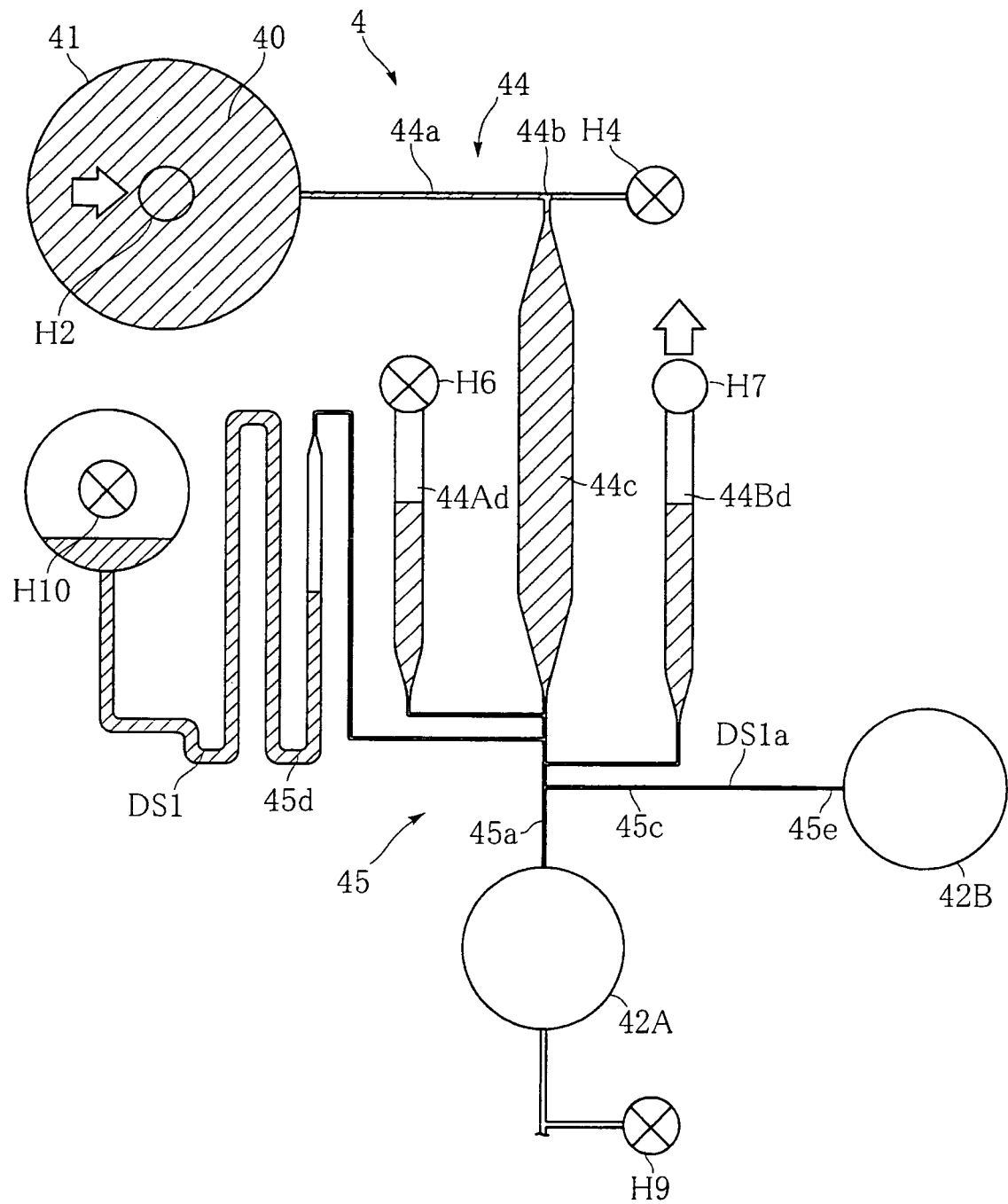
FIG. 31 is a plan view of a principal portion for showing the second dilution step in the liquid feeding method using the cartridge shown in FIG. 26.
Figure 32:
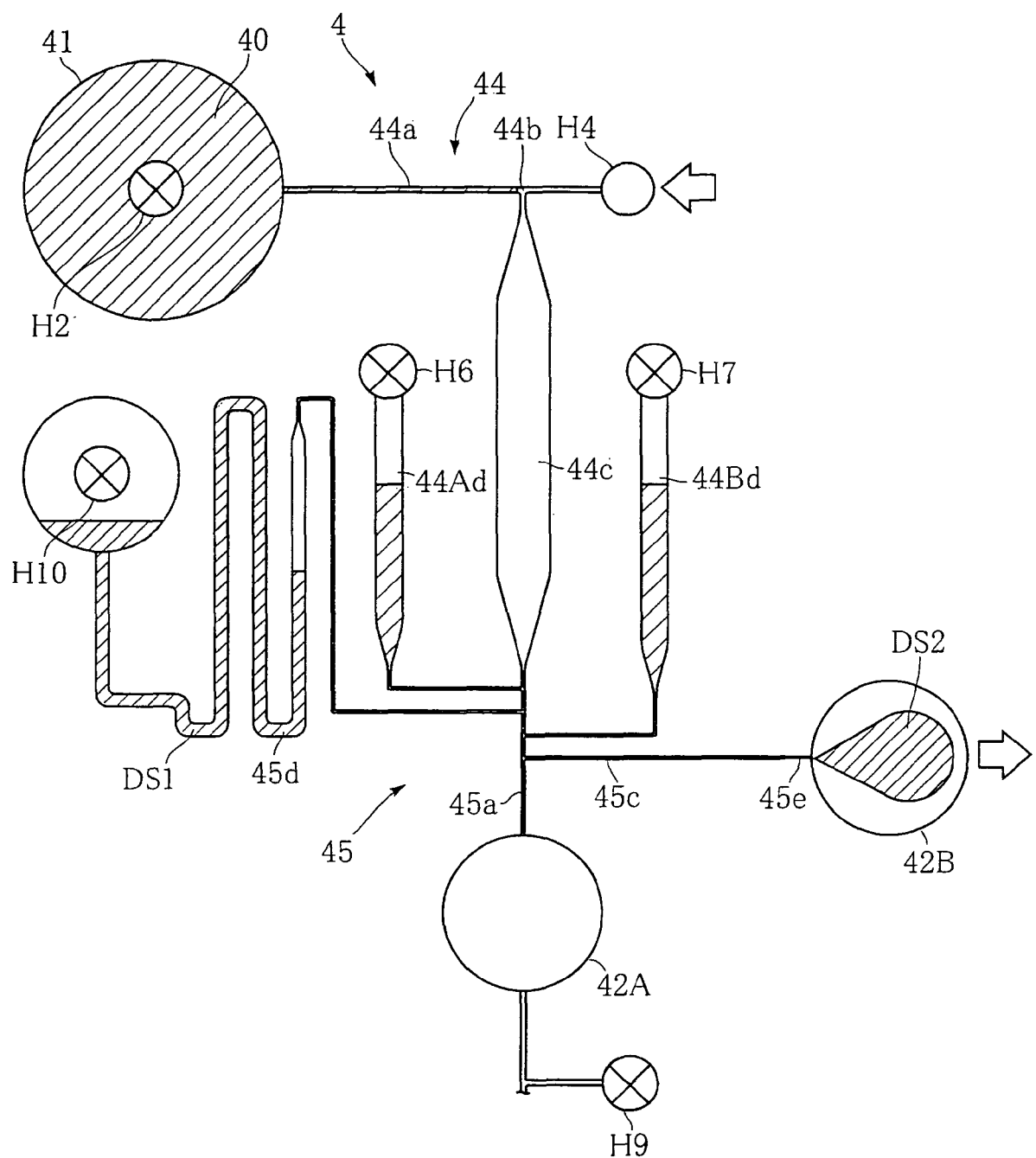
FIG. 32 is a plan view of a principal portion for showing the second dilution step in the liquid feeding method using the cartridge shown in FIG. 26.
Figure 33:
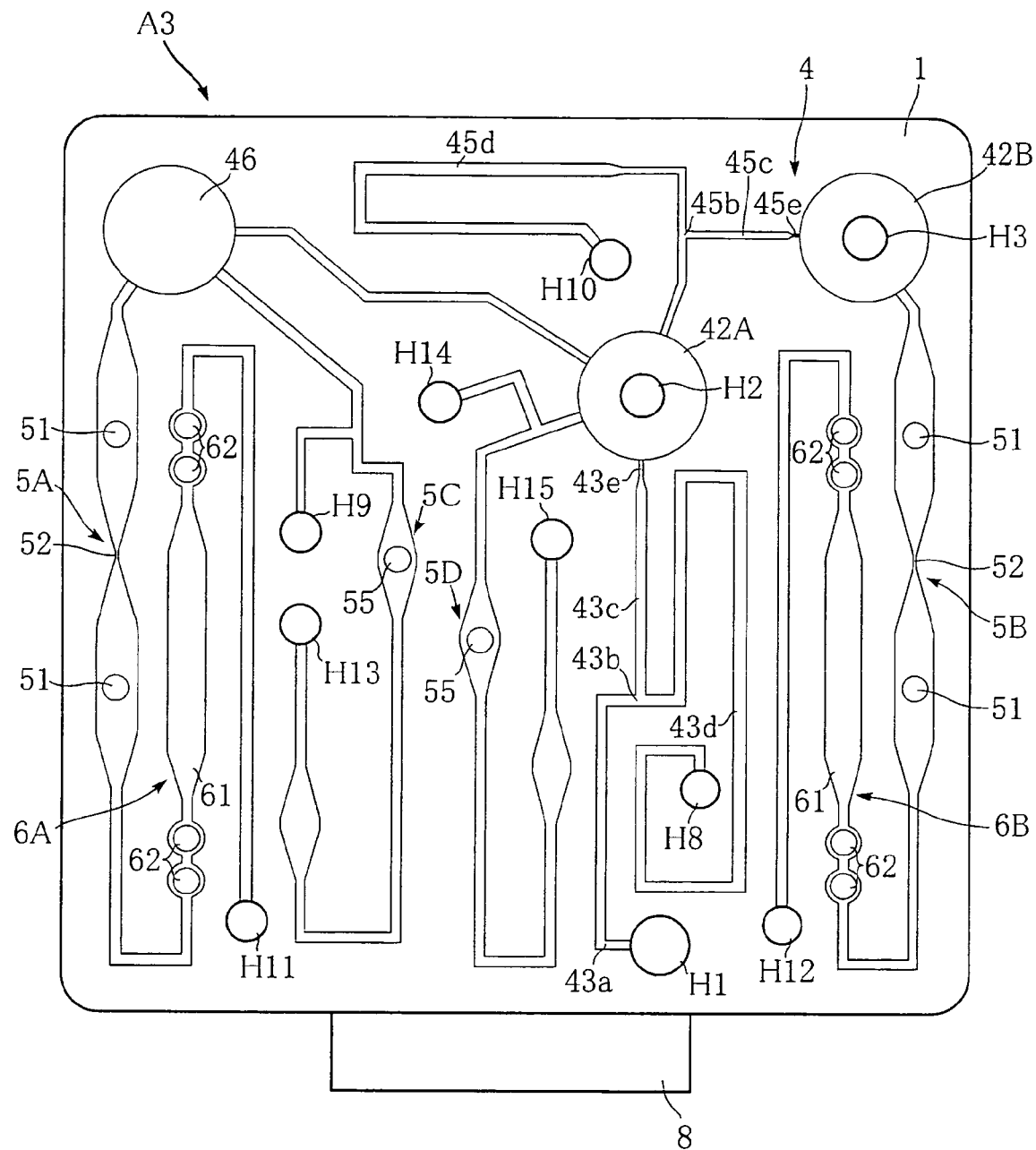
FIG. 33 is a plan view showing a cartridge according to a third embodiment of the present invention.
Figure 34:
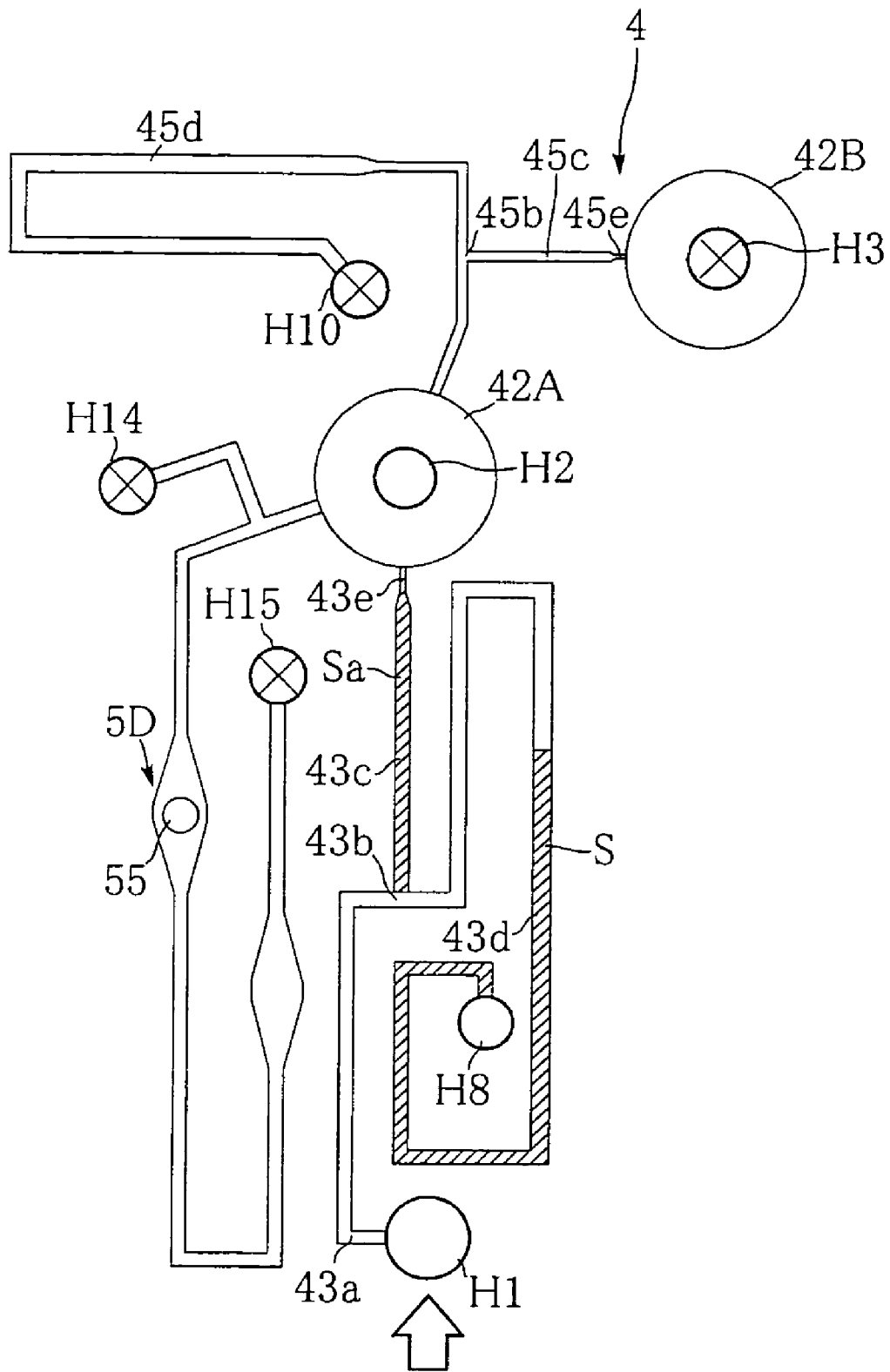
FIG. 34 is a plan view of a principal portion for showing a blood measurement step in a liquid feeding method using the cartridge shown in FIG. 33.
Figure 35:
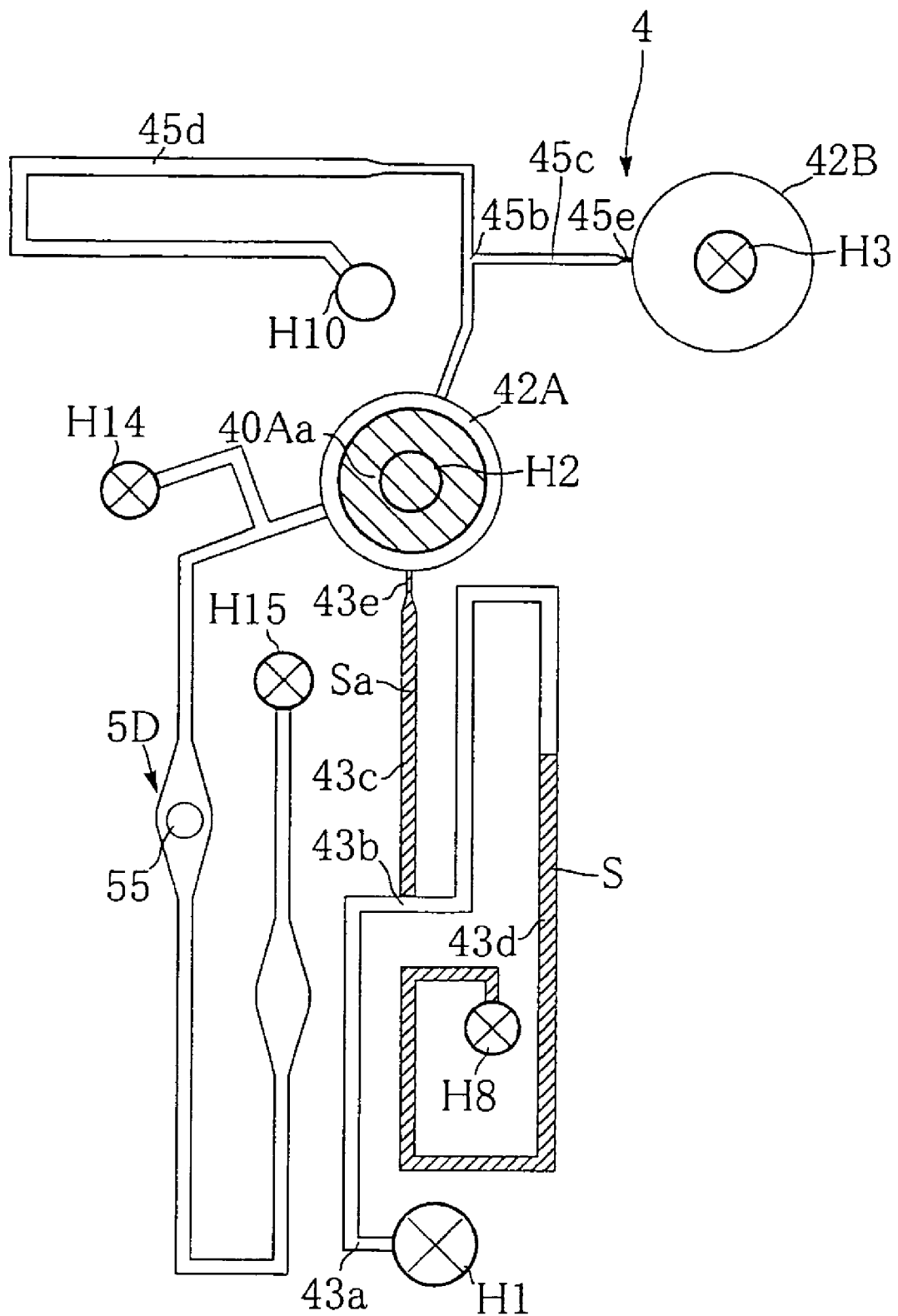
FIG. 35 is a plan view of a principal portion for showing a step of injecting a diluent in the liquid feeding method using the cartridge shown in FIG. 33.
Figure 36:
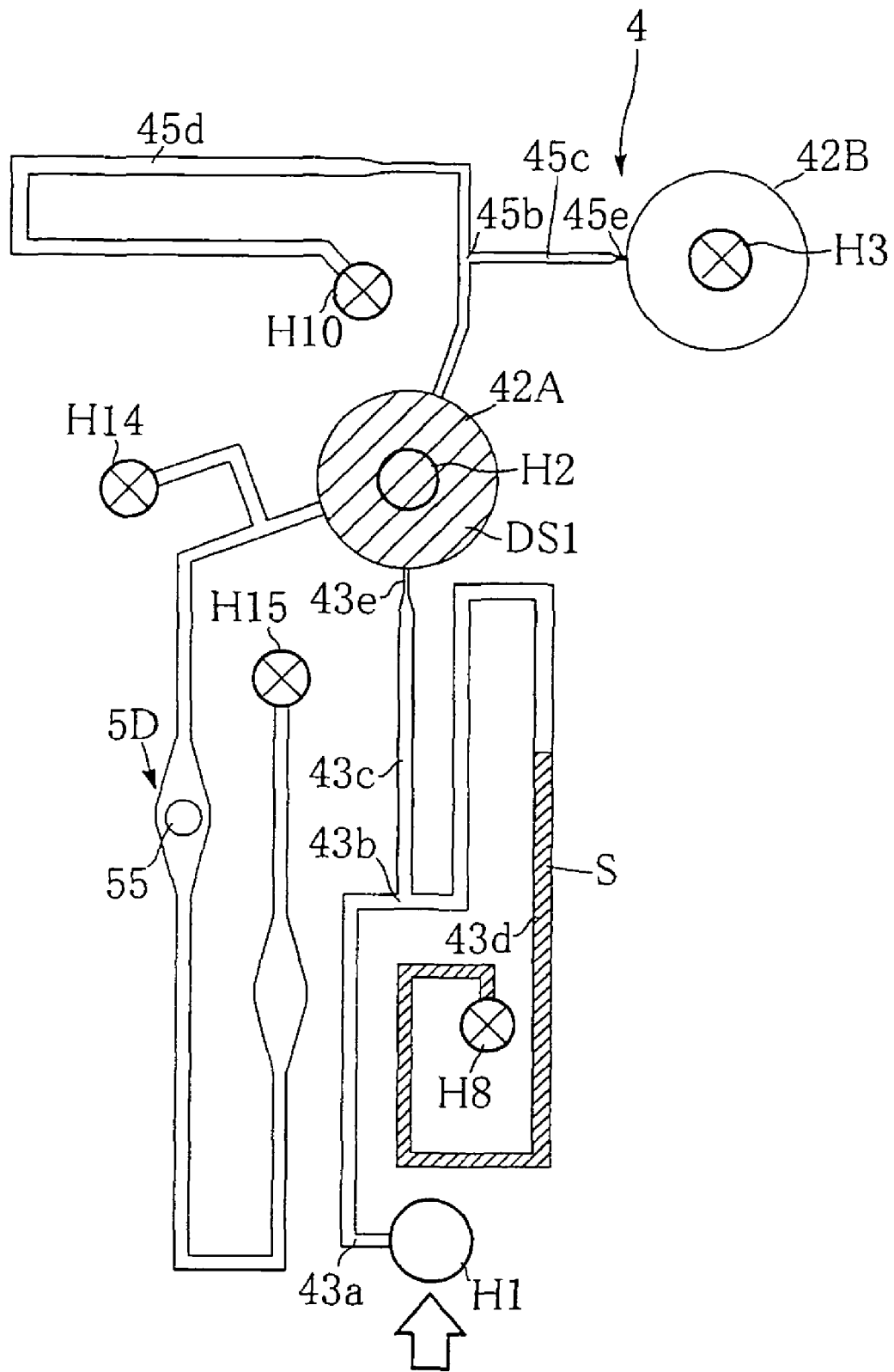
FIG. 36 is a plan view of a principal portion for showing a first dilution step in the liquid feeding method using the cartridge shown in FIG. 33.
Figure 37:
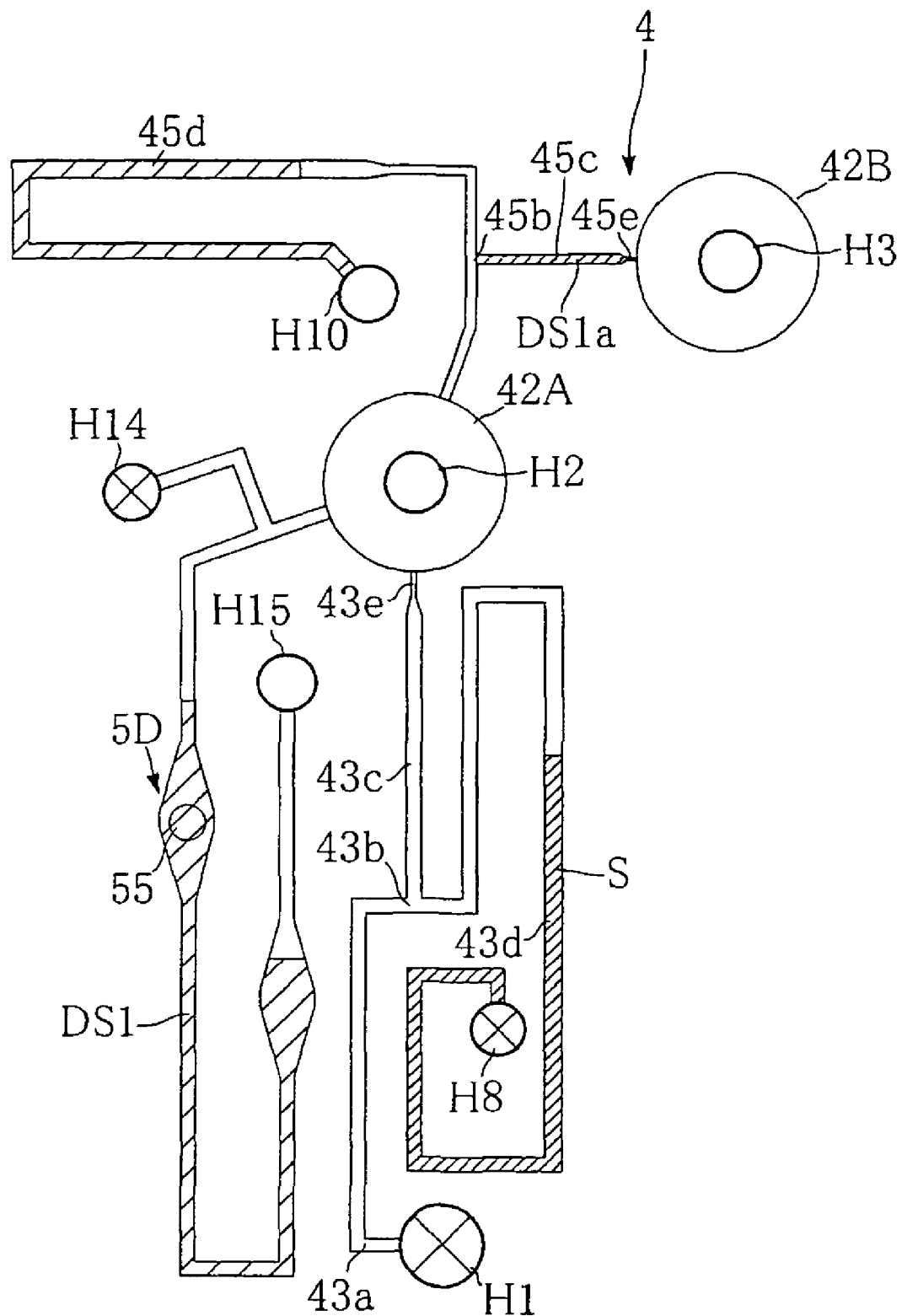
FIG. 37 is a plan view of a principal portion for showing a step of measuring a first blood sample in the liquid feeding method using the cartridge shown in FIG. 33.
Figure 38:
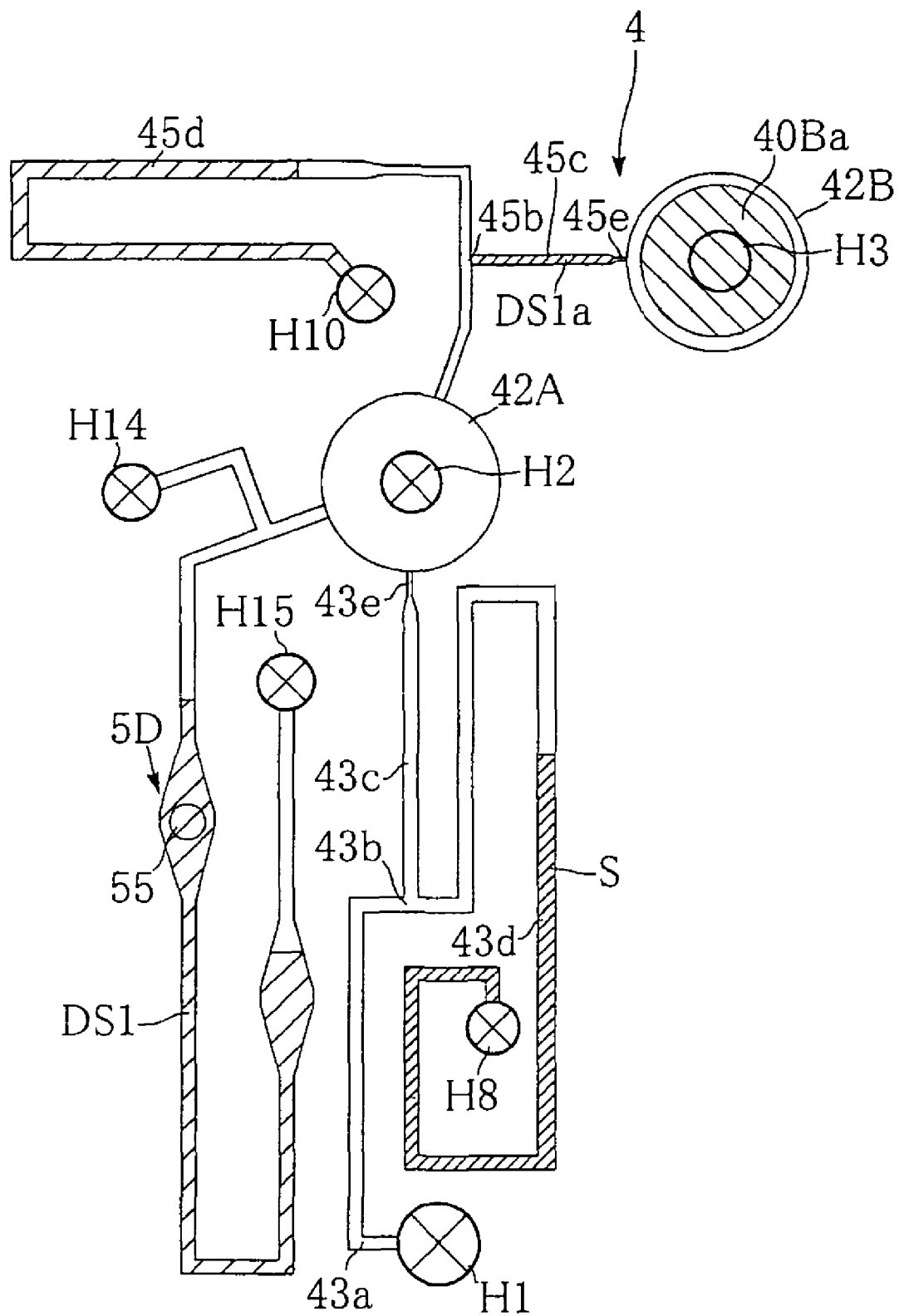
FIG. 38 is a plan view of a principal portion for showing a step of injecting a diluent in the liquid feeding method using the cartridge shown in FIG. 33.
Figure 39:
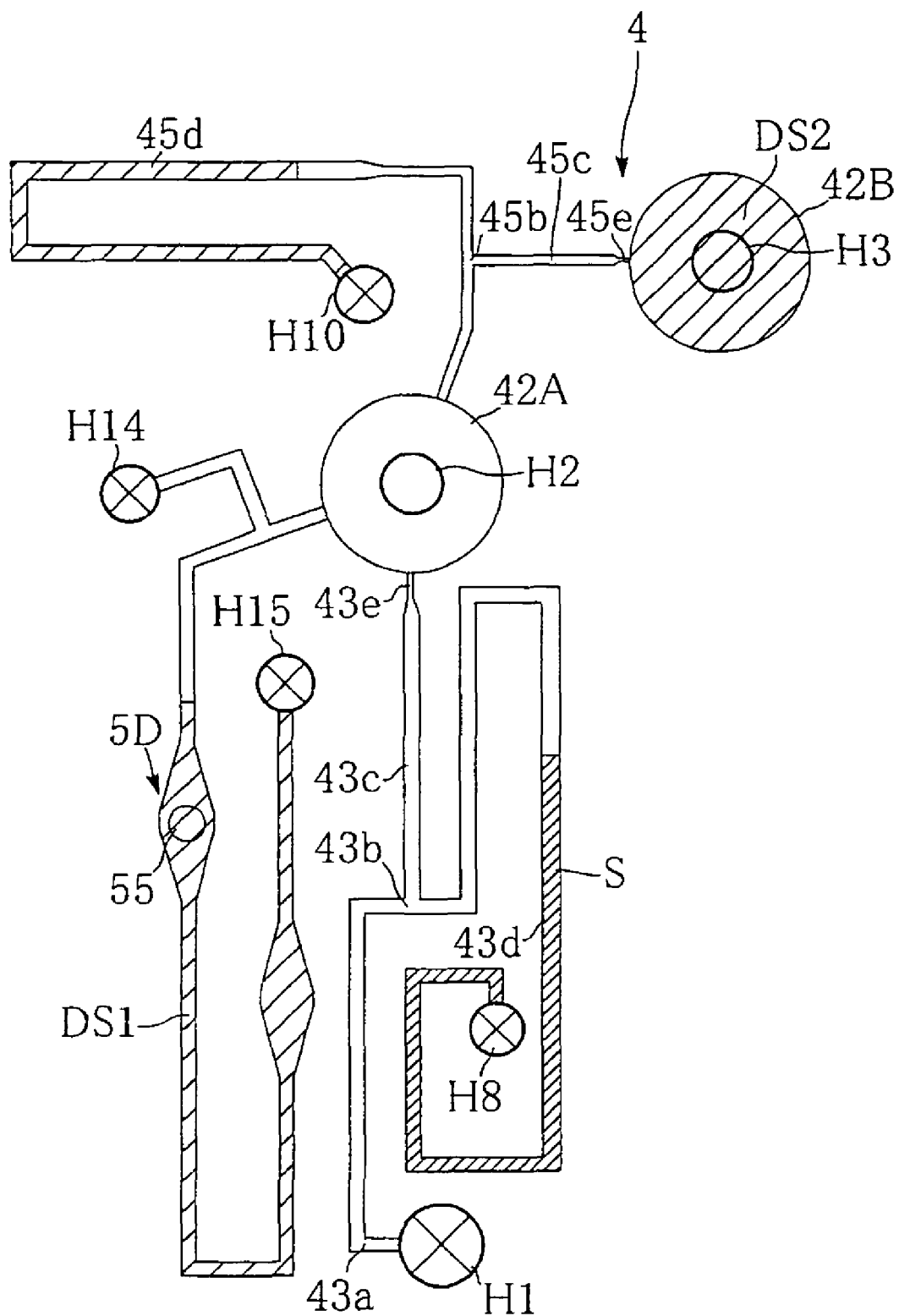
FIG. 39 is a plan view of a principal portion for showing a second dilution step in the liquid feeding method using the cartridge shown in FIG. 33.
Figure 40:
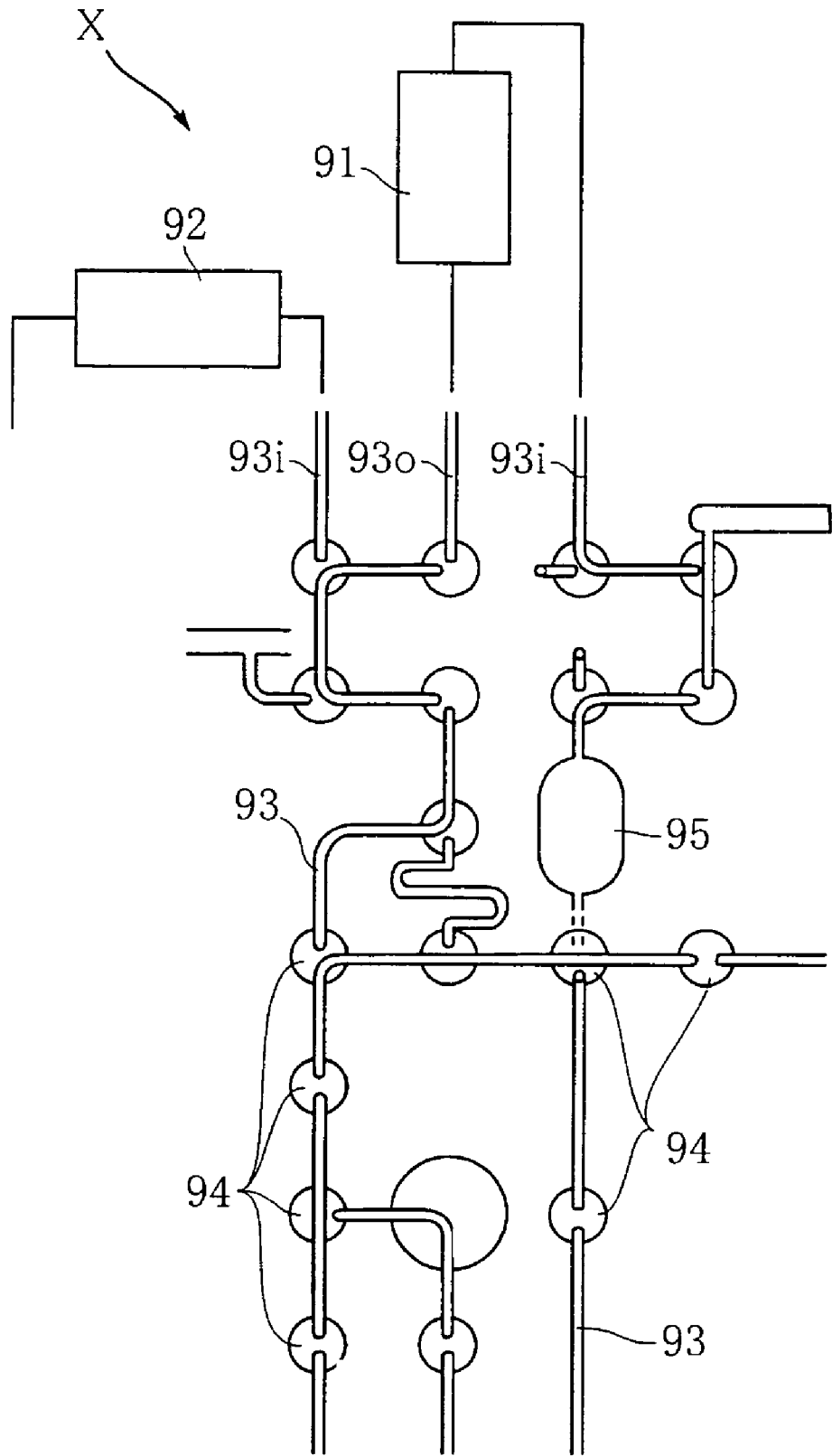
FIG. 40 is a schematic plan view showing an example of conventional liquid feeding method.

The invention claimed is:

1. A liquid feeding method for feeding liquid in a cartridge comprising a first set of flow paths and a second set of flow paths, the first set of flow paths including at least three flow paths having respective first ends connected to each other directly or indirectly via a connection flow path, the method comprising:
    introducing a sample liquid in the first set of flow paths;
    creating a high-pressure state at a second end of a first one of said at least three flow paths of the first set for causing the sample liquid to flow into all three flow paths of the first set;
    forcing a portion of the sample liquid remaining in said first flow path of the first set to flow only into a second one of said at least three flow paths of the first set while retaining another portion of the sample liquid trapped in a third one of said at least three flow paths of the first set;
    forcing said another portion of the sample liquid in said third flow path of the first set to enter a dilution chamber;
    introducing a diluent liquid in the second set of flow paths; and
    causing a portion of the diluent liquid to enter the dilution chamber from the second set of flow paths for mixing with said another portion of the sample liquid.

2. The liquid feeding method according to claim 1, wherein the second ends of at least two of said at least three flow paths of the first set are held in a high-pressure state or a closed state.

3. The liquid feeding method according to claim 1, wherein each flow path in the first and second sets has an inner surface which is hydrophobic with respect to the sample liquid or the diluent liquid.

4. The liquid feeding method according to claim 3, wherein the inner surface of each flow path in the first and second sets has a contact angle of not less than 60 degrees with respect to the sample liquid or the diluent liquid.

5. The liquid feeding method according to claim 1, wherein the second end of said third flow path of the first set is held at atmospheric pressure.

6. The liquid feeding method according to claim 1, wherein the cartridge further comprises a third set of flow paths, the method further comprising:
    causing a portion of sample-diluent mixture from the dilution chamber to enter a additional dilution chamber;
    introducing a diluent liquid into the third set of flow paths; and
    causing a portion of the diluent liquid to enter the additional dilution chamber from the third set of flow paths.

7. The liquid feeding method according to claim 1, wherein the first set of flow paths includes:
    an introduction flow path having a first end at a branch portion and a second end connected to a sample introduction hole, the introduction flow path serving as said first flow path of the first set;
    a measurement flow path having a first end connected to the introduction flow path at the branch portion and a second end connected to the dilution chamber via an orifice, the measurement flow path serving as said third flow path of the first set, the dilution chamber communicating with a first vent hole; and
    an overflow path having a first end connected to the introduction flow path and the measurement flow path at the branch portion and a second end connected to a second vent hole, the overflow path serving as said second flow path of the first set.

8. The liquid feeding method according to claim 1,
    wherein the diluent liquid is supplied from a diluent tank and introduced into all flow paths of the second set that include an introduction flow path, a measurement flow path and an overflow path, and
    only a portion of the diluent liquid trapped in the measurement flow path is forced into the dilution chamber for mixing with said another portion of the sample liquid that is introduced into the dilution chamber, and a portion of the diluent liquid that has entered into the overflow path remain trapped in the overflow path.

* * * * *